United States Patent
Paz et al.

(10) Patent No.: US 8,827,924 B2
(45) Date of Patent: Sep. 9, 2014

(54) DIAGNOSTIC METHODS AND SYSTEMS BASED ON URINE ANALYSIS

(75) Inventors: Ilan Paz, Gush Etzion (IL); Stanley Chimes, Beit Shemesh (IL); Martin Clive Henry Jackson, Ginot Shomron (IL)

(73) Assignee: FlowSense Ltd., Alon Shvut, Gush Etzion (IL)

( * ) Notice: Subject to any disclaimer, the term of this patent is extended or adjusted under 35 U.S.C. 154(b) by 276 days.

(21) Appl. No.: 12/711,221

(22) Filed: Feb. 23, 2010

(65) Prior Publication Data

US 2010/0286559 A1    Nov. 11, 2010

(51) Int. Cl.
*A61B 5/00*    (2006.01)

(52) U.S. Cl.
USPC ............ 600/573; 600/584; 204/400; 700/266

(58) Field of Classification Search
USPC .................... 600/573, 581; 204/400; 700/266
See application file for complete search history.

(56) References Cited

U.S. PATENT DOCUMENTS

| | | | |
|---|---|---|---|
| 3,641,543 A | 2/1972 | Rigby | |
| 3,712,132 A | 1/1973 | Thys et al. | |
| 3,859,854 A | 1/1975 | Dye et al. | |
| 3,870,065 A | 3/1975 | Minns, Jr. | |
| 3,871,229 A | 3/1975 | Fletcher | |
| 3,888,237 A * | 6/1975 | Mori .............................. | 600/350 |
| 4,038,982 A | 8/1977 | Burke et al. | |
| 4,051,431 A | 9/1977 | Wurster | |
| 4,099,412 A | 7/1978 | Nehrbass | |
| 4,261,388 A | 4/1981 | Shelton | |
| 4,321,461 A | 3/1982 | Walter, Jr. et al. | |
| 4,325,483 A | 4/1982 | Lombardo et al. | |
| 4,343,316 A | 8/1982 | Jespersen | |
| 4,448,207 A | 5/1984 | Parrish | |
| 4,484,582 A | 11/1984 | Rottenberg et al. | |

(Continued)

FOREIGN PATENT DOCUMENTS

| | | |
|---|---|---|
| GB | 2389534 | 12/2003 |
| JP | H02151724 | 12/1998 |

(Continued)

OTHER PUBLICATIONS

International search Report for PCT/IL2008/001153, Feb. 26, 2009.

(Continued)

*Primary Examiner* — Max Hindenburg
*Assistant Examiner* — Renee Danega
(74) *Attorney, Agent, or Firm* — Greer, Burns & Crain, Ltd.

(57) ABSTRACT

A diagnostic method and apparatus for detecting at least one change in a urinary parameter indicative of a body malfunction, the method comprising at least semi-continuously monitoring in real time at least one of a sodium level, an oxygen level, a potassium level, and combinations thereof in the urine of a catheterized patient; whereby at least one parameter is monitored so as to detect one or more changes in the at least one parameter to reflect at least one of a fluid state, an electrolyte balance, a kidney state, a kidney perfusion and an organ perfusion in the patient, indicative of the body malfunction in the patient, in which the monitoring is preferably performed through electrodes that are arranged perpendicularly to the flow of urine through a patient's catheter system.

19 Claims, 19 Drawing Sheets

(56) References Cited

U.S. PATENT DOCUMENTS

| | | | |
|---|---|---|---|
| 4,520,667 A | 6/1985 | Nelson | |
| 4,532,936 A | 8/1985 | LeVeen et al. | |
| 4,535,786 A * | 8/1985 | Kater | 600/573 |
| 4,554,687 A | 11/1985 | Carter et al. | |
| 4,559,831 A | 12/1985 | Prestele | |
| 4,650,464 A | 3/1987 | Ruiz et al. | |
| 4,683,748 A | 8/1987 | Carter | |
| 4,718,896 A | 1/1988 | Arndt et al. | |
| 4,740,200 A | 4/1988 | Theeuwes | |
| 4,827,766 A | 5/1989 | Nelson | |
| 4,936,828 A | 6/1990 | Chiang | |
| 4,946,439 A | 8/1990 | Eggers | |
| 5,098,408 A | 3/1992 | Tarzian | |
| 5,186,057 A | 2/1993 | Everhart | |
| 5,267,978 A | 12/1993 | Dirr, Jr. et al. | |
| 5,571,964 A | 11/1996 | Sawada et al. | |
| 5,581,026 A | 12/1996 | Sawada et al. | |
| 5,698,793 A | 12/1997 | Carmichael | |
| 5,704,353 A | 1/1998 | Kalb | |
| 5,769,087 A | 6/1998 | Westphal et al. | |
| 6,372,506 B1 | 4/2002 | Norton | |
| 6,447,684 B2 | 9/2002 | Parekh et al. | |
| 6,640,649 B1 | 11/2003 | Paz | |
| 7,147,606 B1 | 12/2006 | Chang | |
| 7,563,243 B2 | 7/2009 | Mendels | |
| 7,931,630 B2 * | 4/2011 | Nishtala et al. | 604/318 |
| 2003/0045840 A1 | 3/2003 | Burko | |
| 2006/0100743 A1 | 5/2006 | Townsend et al. | |
| 2007/0088333 A1 | 4/2007 | Levin et al. | |
| 2009/0149776 A1 * | 6/2009 | Adams | 600/584 |
| 2010/0022967 A1 | 1/2010 | Mendels | |
| 2010/0094204 A1 * | 4/2010 | Nishtala | 604/66 |
| 2010/0121220 A1 * | 5/2010 | Nishtala | 600/581 |
| 2010/0286667 A1 | 11/2010 | Paz | |

FOREIGN PATENT DOCUMENTS

| | | |
|---|---|---|
| JP | H04032035 | 1/2006 |
| WO | WO0042394 | 7/2000 |
| WO | WO02065912 | 8/2002 |
| WO | WO2004045704 | 6/2004 |
| WO | WO2005057210 | 6/2005 |
| WO | WO2006000764 | 1/2006 |
| WO | WO2009024985 | 2/2009 |
| WO | WO2010041458 | 12/2010 |
| WO | WO2010041563 | 12/2010 |

OTHER PUBLICATIONS

Written Opinion for PCT/IL2008/001153, Feb. 23, 2010.
Brazilian Application PI0008757-2 Office Action.
International Search Report for PCT/IL2006/000065.
Written Opinion for PCT/IL2006/000065.
Chinese application 201010002058.1 Office Action.
Japanese application 2007-551812 Office Action.
International search Report for PCT/IL2000/000027.
International search Report for PCT/IL2011/000185.

* cited by examiner

Preparation of the tip

Heating loop device

166

Fig.1D
L/X microelectrode
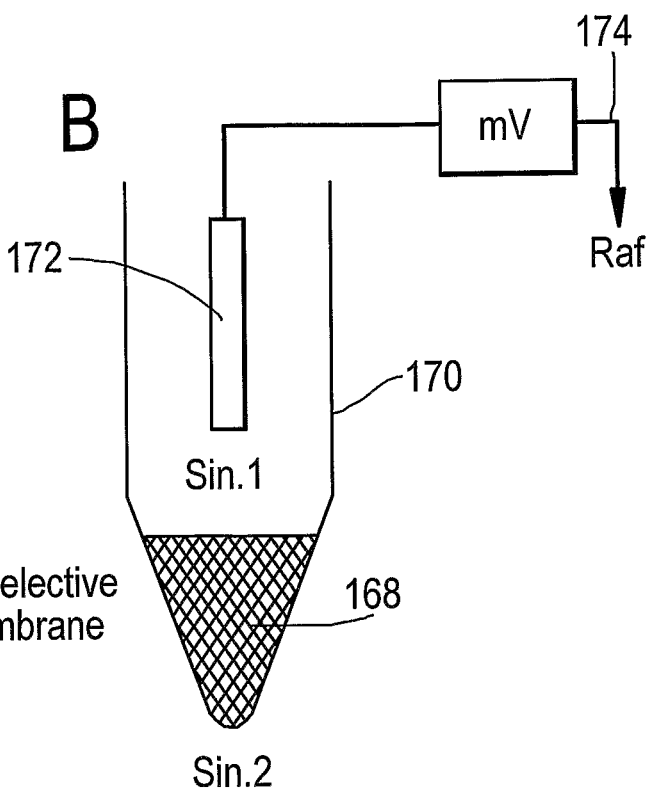
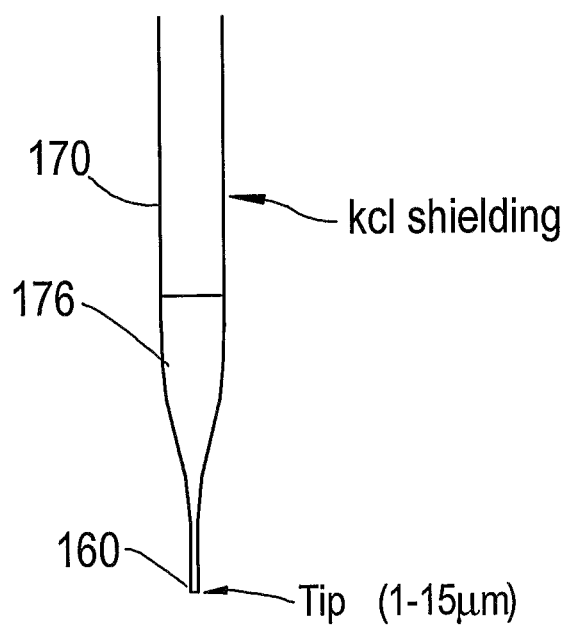

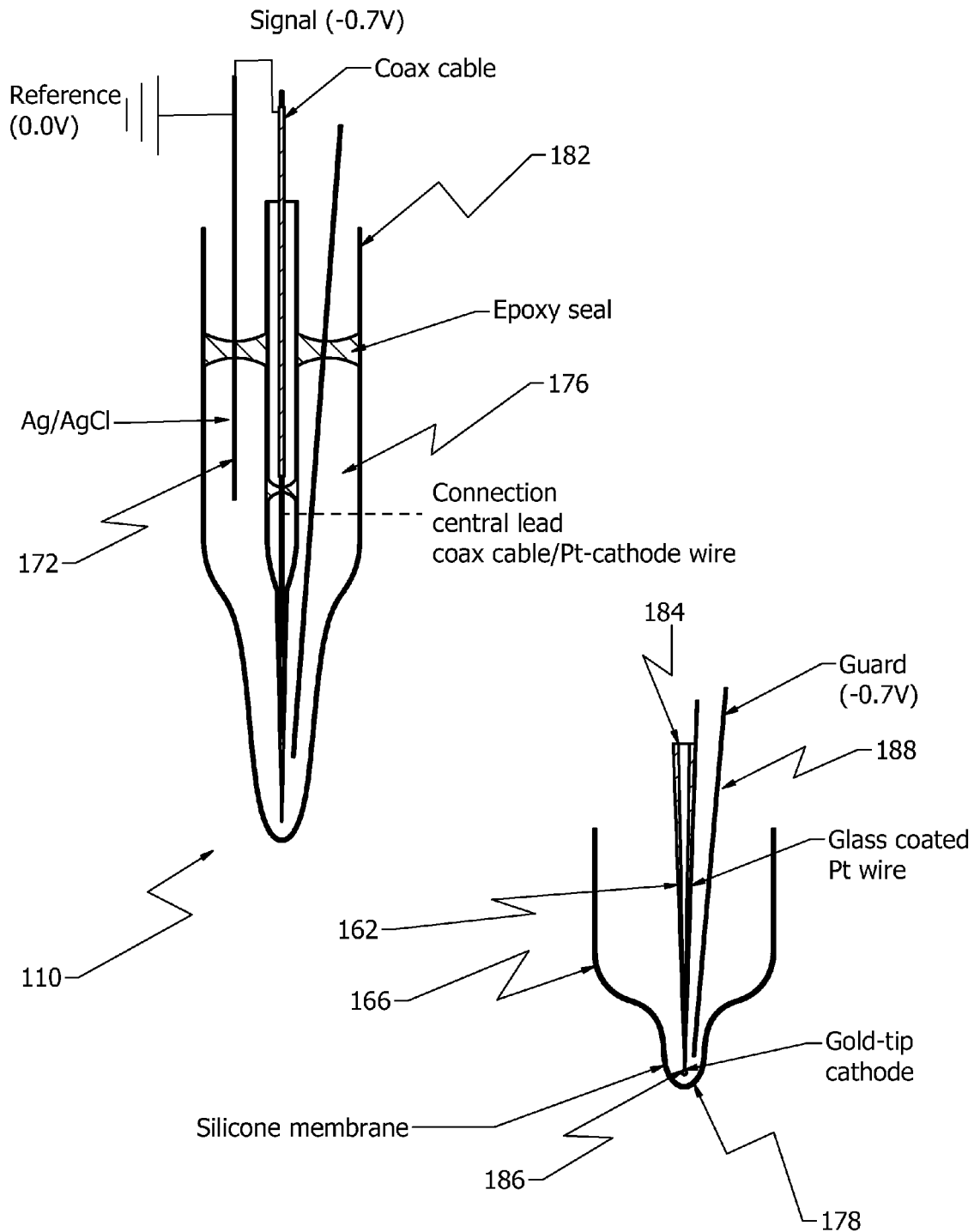
Figure 1F - shape of the 02 microelectrode

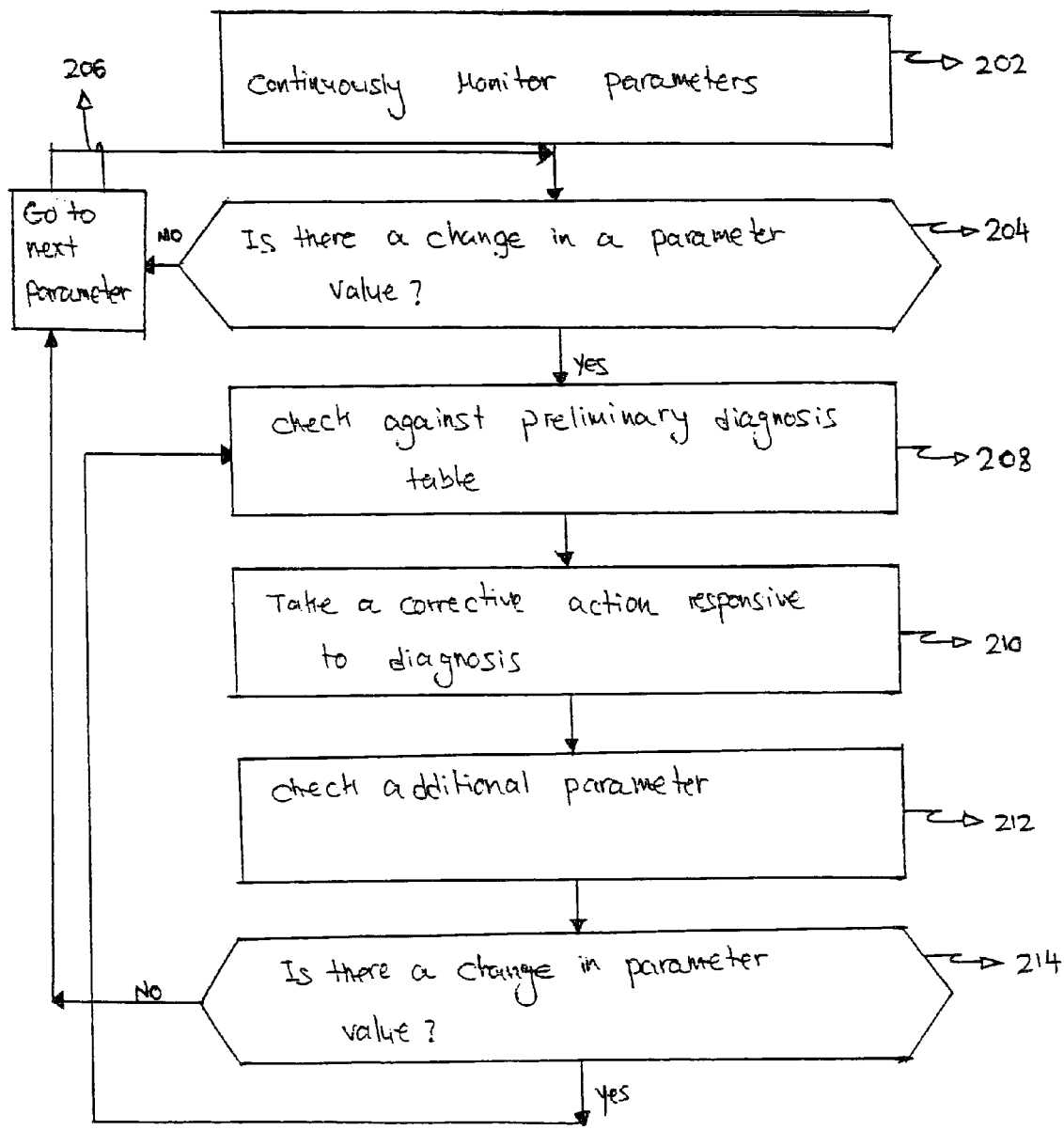

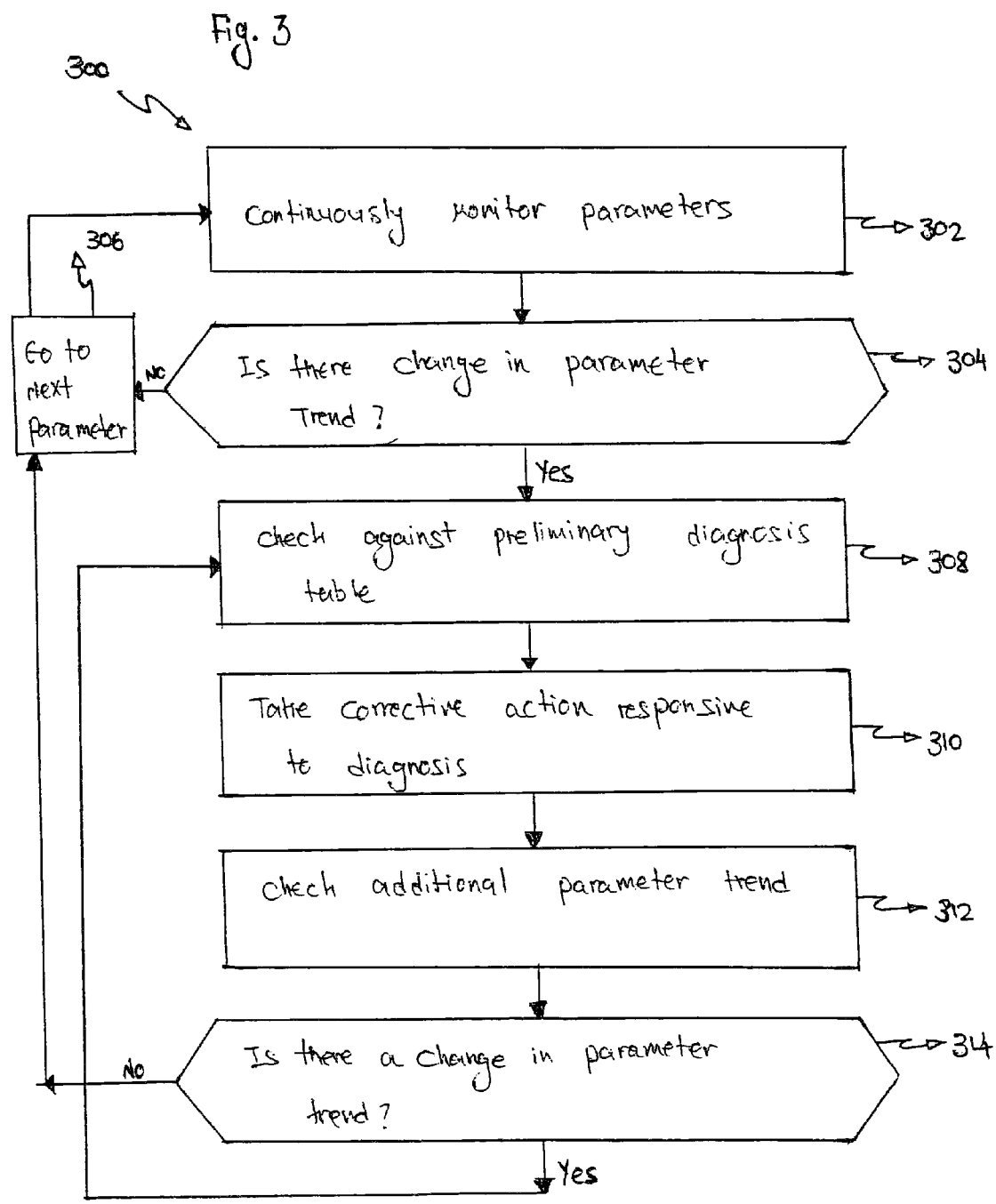

Fig. 4

| Diagnostic Index | Typical Finding in ARF | |
|---|---|---|
| | Prerenal | Intrinsic |
| Renal | | |
| Fractional excretion of sodium (%)[a] | <1 | >1 |
| $(U_{Na} * P_{Cr})/ (P_{Na} * U_{Cr}) * 100$ | | |
| Urine sodium concentration (mmol/L) | <10 | >20 |
| Urine creatinine to plasma creatinine ratio | >40 | <20 |
| Urine urea aitrogen to plasma urea aitrogen ratio | >8 | <3 |
| Urine specific gravity | >1.020 | ~1.010 |
| Urine osmolarity (mosmol/Kg $H_2O$) | >500 | ~300 |
| Plasma BUN/creatinine ratio | >20 | <10-15 |
| Renal failure index $U_{Na}/(U_{Cr}/P_{Cr})$ | <1 | >1 |
| Urinary sediment | Hyaline cases | Muddy Brown Granular casts |

[a] Most sensitive indices.

Note: $U_{Na}$ urine sodium concentration; $P_{Cr}$ plasma creatinine concentration; $P_{Na}$ Plasma sodium concentration; $U_{Cr}$ urine creatinine concentration; BUN. Blood urea nitrogen.

Fig.11

| | |
|---|---|
| Reverse Causative Renal Insult | |
| Ischemic ARF | Restore systemic hemodynamics and renal perfusion |
| Nephrotoxic ARF | Eliminate nephrotoxins. Consider specific measures (e.g. forced alkaline diuresis chelnrors : see text) |
| Prevention and Treatment of Compucations | |
| Intravascular volume overload | Salt (1-2 g/d) and water (usually <L/d) restriction. Diuretics (usually loop blockers = thiazide). Ultrafiltration or dialysis |
| Hyponatremia | Restriction of enteral free water intake (<1L/d) Avoid hypotonic intravenous solutions |
| Hyperkalemia | Restriction of dietary $K^+$ intake (usually 40 mmol/d) Eliminate $K^+$ supplements and $K^+$-sparing diuretics Potassium-binding ion exchange resins (e.g., sodium polystyrene sulphonate) Glucose (50 mL of 50% dextrose) and insulin (10 units regular) Sodium bicarbonate (usually 50-100 mmol) Calcium gluconate (10 mL of 10% solution over 5 min.) Dialysis (with low $K^+$ dialysate) |
| Metabolic acidosis | Restriction of dietary protein (usually 0.6 g/kg per day of high biologic value) Sodium bicarbonate (maintain serum bicarbonate > 15 mmol/L or arterial pH <7.2) Dialysis |
| Hyperphosphatemia | Restriction of dietary phosphate intake (usually <800 mg/d) Phosphate binding agents (calcium carbonate, aluminum hydroxide |
| Hypocalcemia | Calcium carbonate (if symptomatic or if sodium bicarbonate to be administered) Calcium gluconate (10-20 mL of 10% solution) |
| Hypermagnesemia | Discontinue $Mg^{2+}$- containing antacids |
| Hyperuricemia | Treatment usually not necessary (if < 890 μmol/L (<15 mg/dL)) |
| Nutrition | Restriction of dietary protein (~0.6g/kg per day) Carbohydrate (~ 100 g/d) Enteral or parenteral nutrition (if recovery prolonged or patient very catabolic) |
| Indications for dialysis | Clinical evidence (symptoms or signs) of uremia Intractable Intravascular volume overload Hyparkalemia or severe acidosis resistant to conservative measures ?Prophylactic dialysis when urea >100-150 mg/dL or creatinine >8-10mg/dL |

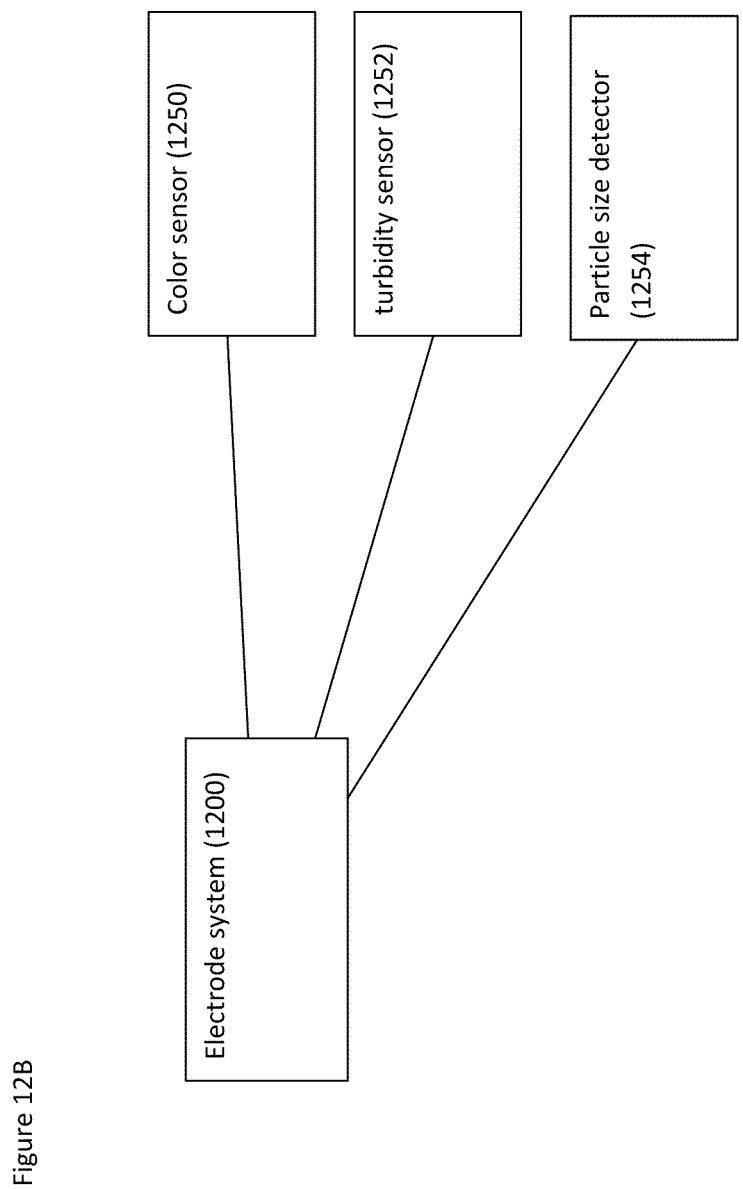

DIAGNOSTIC METHODS AND SYSTEMS BASED ON URINE ANALYSIS

This Application claims priority as a Continuation-in-Part from PCT Application No. PCT/IL2008/001153, filed on Aug. 24, 2008, which claims priority from Israeli Application No. IL185477, filed on 23 Aug. 2007 and from Israeli Application No. IL193591, filed on 21 Aug. 2008, all of which are hereby incorporated by reference as if fully set forth herein.

FIELD OF THE INVENTION

The present invention relates to systems and methods for early detection of body malfunctions in a patient based on real time monitoring of urinary parameters or urine from a catheterized patent, indicative of changes of state in the human body.

BACKGROUND OF THE INVENTION

The kidney is an organ which performs several functions in a mammalian body. It receives approximately 20% of the blood flow from cardiac output. The kidney acts as a filter and normally excretes metabolic and foreign waste products in urine at a rate proportional to the blood flow received from the heart. The excretory function serves, inter alia, to maintain fluid and electrolyte homeostasis. Additionally, the kidney has a gluconeogenesis function and also produces hormones and enzymes.

Urine comprises, water, nitrogenous waste, uric acid, electrolytes and other matter. The urinary output rate is typically measured from the bladder. Changes in the urinary output rate may be indicative of one or more conditions including renal failure.

Acute renal failure may be indicative of one or more of the following conditions:
Prerenal failure (hypoperfusion);
Renal failure (intrinsic); and
Postrenal failure (obstructive).

Prerenal failure is indicative of decreased perfusion without cellular injury, such that the renal tubular and glomerular functions are intact and reversible if the underlying cause is corrected in time.

To date, there are very few reliable methods, if any, for real-time diagnosis of prerenal failure. Thus, all too often, by the time the patient is diagnosed as suffering from prerenal failure, either or both of the kidneys are severely damaged.

Sustained prerenal azotemia is the main factor that predisposes patients to ischemia-induced acute tubular necrosis.

In the case of postrenal failure, it is important to verify if there is any obstruction of the ureters or urethra, since the potential for recovery may be inversely related to the duration of the obstruction.

Renal failure may be classified according to the primary kidney structure suffering the injury, the structure normally being one of tubular, insterstitium, vessel and glomerulus.

To date, renal failure is diagnosed by performing blood tests, urine analysis, by renal indices and physical examination including scans such as ultrasound, Doppler and others However, it should be noted that, for a large part, the blood and urine tests are performed off-line with a delay. This delay is often critical and may significantly reduce the potential for recovery.

Normally, the blood tests and urine tests performed include CBC BUN/creatine, electrolytes, uric acid, PT/PTT and CK.

An offline test to differentiate between prerenal and renal failure may include checking specific gravity and urinary sodium levels and other parameters. Differences in the values of these parameters may be used to differentiate between these two states.

Nephrotoxins, which have a deleterious effect on the renal perfusion, include, but are not limited to aminoglycosides, NSAIDs and amphotericin.

One of the most troublesome of all problems in critically ill patients is maintenance of adequate body fluid which includes proper balance between fluid input and fluid output. To date, most patients that are hospitalized in the Intensive Care Unit (ICU) are monitored by continuous measurement of several hemodynamic parameters, such as heart rate, invasive blood pressure measurement, central venous pressure (CVP) and occasionally, wedge pressure.

It is well known that one of the most important parameters that reflects proper organ perfusion is the hourly urine output. However, currently the tools and systems that are used are not precise enough. One outcome of this is the high occurrence of acute renal failure (ARF) in ICU's. This complication occurs in a significant percentage of critically ill patients. The most common underlying etiology is acute tubular necrosis, usually precipitated by hypoperfusion and/or nephrotoxic agents. On the other hand, overzealous use of fluid may result in fluid overload, pulmonary edema and, acute respiratory distress syndrome. (ARDS)

The following are explanations of terms and diseases referred to herein.

ARF (Acute Renal Failure)

Acute Renal Failure (ARF) is a syndrome characterized by a rapid decline in the glomerular filtration rate (hours to days), retention of nitrogenous waste products, and perturbation of extracellular fluid volume and electrolyte and acid-base homeostasis. ARF is a complication of approximately 5% of hospital admissions and of up to 30% of admissions to intensive care units. Oliguria (urine output<400 ml_/d) is a frequent but not invariable clinical feature (50%) of ARF. ARF is usually asymptomatic and is diagnosed when biochemical monitoring of hospitalized patients is elevated and may be diagnosed by monitoring hospitalized patients, and is indicated by increases in blood urea and creatinine concentrations. It may complicate a wide range of diseases, which for purposes of diagnosis and management are conveniently divided into three categories:

(1) Diseases that cause renal hypoperfusion without compromising the integrity of renal parenchyma (prerenal ARF, prerenal azotemia) (55%), (2) Diseases that directly involve renal parenchyma (intrinsic renal ARF, renal azotemia) (40%);

(3) Diseases associated with urinary tract obstruction (postrenal ARF, postrenal azotemia) (5%).

Most incidences of ARF are reversible, the kidney being relatively unique among major organs in its ability to recover from almost complete loss of function. Nevertheless, ARF is associated with high incidence of in-hospital morbidity and mortality rates, in large part due to the serious nature of the illnesses that precipitate the ARF. Severe cases may show clinical or pathologic evidence of acute tubular necrosis (ATN). In contrast, nephropathy classically presents itself as an acute disorder (onset within 24 to 48 hours) but is reversible. GFR (Glomerular Filtration Rate)

The GFR was originally determined by injecting insulin into the plasma. Since inulin is not reabsorbed by the kidney after glomerular filtration, its rate of excretion is directly proportional to the rate of filtration of water and solutes across the glomerular filter. In clinical practice however, creatinine clearance is used to measure GFR. Creatinine is an endogenous molecule, synthesized in the body, which is freely filtered by the glomerulus (but also secreted by the renal tubules in very small amounts). Creatinine clearance is therefore a close approximation of the GFR. The GFR is typically recorded in milliliters per minute (ml/min). Example: A person has a plasma creatinine concentration of 0.01 mg/ml and in 1 hour the excretes 75 mg of creatinine in the urine. The GFR is calculated as M/P (where M is the mass of creatinine excreted per unit time and P is the plasma concentration of creatinine).

Renal failure is the condition in which the kidneys fail to function properly. Physiologically, renal failure is described as a decrease in the glomerular filtration rate. Clinically, this manifests in an elevated serum creatinine. It can broadly be divided into two categories: acute renal failure and chronic renal failure.

Chronic Renal Failure (CRF) develops slowly and gives few symptoms initially. It can be the complication of a large number of kidney diseases, such as IgA nephritis, glomerulonephritis, chronic pyelonephritis and urinary retention. End-stage renal failure (ESRF) is the ultimate consequence, in which case dialysis is generally required until a donor for a renal transplant is found.

Acute Renal Failure (ARF) is, as the name implies, a rapidly progressive loss of renal function, generally characterised by oliguria (decreased urine production, quantified as less than 400 ml_per day in adults, less than 0.5 ml_/kg/h in children or less than 0.1 mUkg/h in infants), body water and body fluids disturbance and electrolyte derangement. An underlying cause must be identified to arrest the progress, and dialysis may be necessary to bridge the time gap required for treating these underlying causes.

Acute renal failure can be present concurrently with chronic renal failure. This is called acute-on-chronic renal failure (AoCRF). The acute part of AoCRF may be reversible and the aim of treatment, as in ARF, is to return the patient to their baseline renal function, which is typically measured by serum creatinine. AoCRF, like ARF, can be difficult to distinguish from chronic renal failure, particularly if the patient has not been followed by a physician and no baseline (i.e., past record) blood work is available for comparison.

Before the advancement of modern medicine, renal failure might have been referred to as uremic poisoning. Uremia was the term used to describe the contamination of the blood with urine. Starting around 1847 this term was used to describe reduced urine output, now known as oliguria that was thought to be caused by the urine mixing with the blood instead of being voided through the urethra.

Prerenal Azotemia

Prerenal azotemia is relatively common, especially in hospitalized patients. The kidneys normally filter the blood. When the volume or pressure of blood flow through the kidney drops, blood filtration also drops drastically, and may not occur at all. Waste products remain in the bloodstream and little or no urine is formed, even though the internal structures of the kidney are intact and functional.

Lab tests show that nitrogen-type wastes, such as creatinine and urea, are accumulating in the body (azotemia). These waste products act as poisons when they accumulate, damaging tissues and reducing the ability of organs to function. The build-up of nitrogen waste products and accumulation of excess fluid in the body are responsible for most of the symptoms of prerenal azotemia and acute renal failure.

Prerenal azotemia is the most common form of kidney failure seen in hospitalized patients. Any condition that reduces blood flow to the kidney may cause it, including loss of blood volume, which may occur with dehydration, prolonged vomiting or diarrhea, bleeding, burns, and other conditions that allow fluid to escape circulation.

Conditions in which the volume is not lost, but in which the heart cannot pump enough blood, or the blood is pumped at low volume, also increase the risk of prerenal azotemia. These conditions include shock, such as septic shock, heart failure, and conditions where the blood flow to the kidney is interrupted, such as trauma to the kidney, various surgical procedures, renal artery embolism, and other types of renal artery occlusion.

SUMMARY OF SOME EMBODIMENTS

The present invention overcomes the background art by providing, in at least some embodiments, systems and methods for detecting body states using continuous, real time urine monitoring of analytes, other than creatinine and urea. The systems and methods of the present invention also relate to the use of measurements of the analytes together with measurement of urine output and urine flow, according to at least some embodiments of the present invention.

The present invention, according to at least some embodiments, relates to systems and methods for early detection of body malfunctions in a patient based on real time monitoring of urinary parameters or urine from a catheterized patent, indicative of changes of state in the human body.

More particularly, the present invention, according to at least some embodiments, relates to a diagnostic method, system and apparatus for detecting, in real time, at least one change in a urinary parameter indicative of a body malfunction.

Thus according to at least some embodiments of the present invention there is now provided, a diagnostic method and apparatus for detecting at least one change in a urinary parameter indicative of a body malfunction, the method comprising at least semi-continuously monitoring in real time at least one of a sodium level, an oxygen level, a potassium level, and combinations thereof in the urine of a catheterized patient; whereby at least one parameter is monitored so as to detect one or more changes in the at least one parameter to reflect at least one of a fluid state, an electrolyte balance, a kidney state, a kidney perfusion and an organ perfusion in the patient, indicative of the body malfunction in the patient, in which the monitoring is preferably performed through electrodes that are arranged perpendicularly to the flow of urine through a patient's catheter system, and preferably also in-line to the flow of urine.

The term "semi-continuously" is intended to denote a monitoring at regular intervals of less than once a day, e.g., once every 10-30 minutes or even once every 8 hours, e.g., 3 times a day.

Thus, in preferred embodiments of the present invention, the at least semi-continuous monitoring is carried out at least once every hour.

In more preferred embodiments, the at least semi-continuous monitoring is carried out at least once every half hour.

In especially preferred embodiments of the present invention the at least semi-continuous monitoring is carried out at least once every ten minutes.

In preferred embodiments of the present invention the diagnostic method comprises at least semi-continuously monitoring, in real time, the sodium level of the catheterized patient.

In other preferred embodiments of the present invention the method comprises at least semi-continuously monitoring, in real time, the oxygen level of the catheterized patient.

In some preferred embodiments of the present invention the method comprises at least semi-continuously monitoring, in real time, the potassium level of the catheterized patient.

In especially preferred embodiments of the present invention there is provided a diagnostic method as described above for detecting at least one change in a urinary parameter indicative of a body malfunction, the method comprising: a. continuously monitoring and transmitting urine output and urine flow rates of a catheterized patient; b. continuously monitoring in real time at least one of a sodium level, an oxygen level, a potassium level, and combinations thereof in the urine of the catheterized patient; whereby at least one parameter is monitored so as to detect one or more changes in the at least one parameter to reflect at least one of a fluid state, an electrolyte balance, a kidney state, a kidney perfusion and an organ perfusion in the patient, indicative of the body malfunction in the patient.

In the especially preferred embodiments, the method preferably utilizes a low fluid flow metering device.

Preferably the method further comprises continuously monitoring and graphically representing, in real time, fluctuations in renal urine flow and renal urine output.

Thus the present invention preferably provides a diagnostic method for early prognosis of a disease affiliated with abnormal body fluid status.

Preferably the low fluid flow metering device incorporates a drop generator and a droplet counter.

In especially preferred embodiments of the present invention alarm means are also provided.

In further preferred embodiments of the present invention the method further comprises monitoring at least one of an osmolarity, pH, conductivity, bicarbonate concentration, carbonate concentration, carbon dioxide concentration, and phosphate concentration of the urine in a kidney or ureter.

In the method of the present invention, the parameter comprises a change in at least one of a concentration of an electrolyte and a quantity of an electrolyte and a volumetric change of urine output.

Thus the parameter can be indicative of a pre-renal failure.

The invention also provides a diagnostic method as defined above, for detecting at least one change in a trend of a urinary parameter indicative of a body malfunction, the method comprising at least semi-continuously monitoring in real time at least one of a sodium level, an oxygen level, a potassium level, and combinations thereof in the urine of a catheterized patient; whereby at least one dynamic trend is monitored so as to detect one or more changes in the at least one dynamic trend, to reflect at least one of a fluid state, an electrolyte balance, a kidney state, a kidney perfusion and an organ perfusion in the patient, indicative of the body malfunction in the patient.

In another aspect of the present invention, there is provided a system for detecting at least one change in a urinary parameter indicative of a body malfunction, the system comprising: a. a urinary flow apparatus for continuously monitoring and transmitting urine output and urine flow rates of a catheterized patient; b. a real-time electrolyte concentration measuring apparatus for continuously monitoring in real time at least one of a sodium level, an oxygen level, a potassium level, and combinations thereof in the urine of a catheterized patient; wherein the system is adapted to monitor at least one parameter so as to detect one or more changes in the at least one parameter to reflect at least one of a fluid state, an electrolyte balance, a kidney state, a kidney perfusion and an organ perfusion in the patient, indicative of the malfunction in the patient.

In preferred embodiments of the system the urinary flow apparatus comprises a low fluid flow metering device.

Preferably the urinary flow apparatus further comprises a computerized system for continuously monitoring and graphically representing in real time fluctuations in renal urine flow and renal urine output.

In some preferred embodiments of the present invention the real-time electrolyte concentration apparatus comprises at least one of an oxygen electrode for monitoring oxygen concentration in urine; a sodium electrode for monitoring sodium concentration in urine; a potassium electrode for measuring potassium concentration in urine; an electrolyte electrode for measuring the concentration of at least one other metabolite in urine; and a pH electrode for measuring pH of urine.

In preferred embodiments of the present invention at least one of the electrodes is a microelectrode.

In other preferred embodiments of the present invention at least one of the electrodes is a mini-electrode.

In other preferred embodiments of the present invention at least one of the electrodes is a macro-electrode.

In some preferred embodiments of the present invention at least one of the electrodes is positioned at a joint between the catheter of the catheterized patient and a tube leading therefrom.

In other preferred embodiments of the present invention at least one of the electrodes is positioned along a tube leading from the catheter of the catheterized patient.

In yet another preferred embodiment of the present invention at least one of the electrodes is positioned at a joint between tubing leading from the catheter of the catheterized patient and the urinary flow apparatus.

In other preferred embodiments of the present invention at least one of the electrodes is positioned in the urinary flow apparatus.

In yet another preferred embodiment of the present invention at least one of the electrodes is positioned in a urine collection bag.

In yet another preferred embodiment of the present invention at least one of the electrodes is positioned in the catheter.

In preferred embodiments, the at least semi-continuous monitoring is carried out at least once every hour.

In other preferred embodiments, the at least semi-continuous monitoring is carried out at least once every half hour.

In yet other preferred embodiments the at least semi-continuous monitoring is carried out at least once every ten minutes.

The invention also provides a system as defined above for detecting at least one change in a trend of a urinary parameter indicative of a body malfunction, the system comprising: a. a urinary flow apparatus for continuously monitoring and transmitting urine output and urine flow rates of a catheterized patient; b. a real-time electrolyte concentration measuring apparatus for continuously monitoring in real time at least one of a sodium level, an oxygen level, a potassium level, and combinations thereof in the urine of a catheterized patient; wherein the system is adapted to monitor at least one dynamic trend so as to detect one or more changes in the at least one dynamic trend to reflect at least one of a fluid state, an electrolyte balance, a kidney state, a kidney perfusion and an organ perfusion in the patient, indicative of the malfunction in the patient.

Both sodium and water freely filtrate from the glomerular capillaries into Bowman's space because they have low molecular weights and circulate in the plasma as a free form. The Na+ and water undergo considerable reabsorption, normally more than 99%, but no secretion. Most renal energy utilization goes to accomplish this enormous reabsorptive task. The bulk water and Na+ reabsorption (about two thirds) occurs in the proximal tubule, but the major hormonal control of reabsorption is exerted on the distal convoluted tubules and collecting duct.

The Na+ reabsorption is an active process occurring in all tubular segments except the descending limb of the loop of Henle, while water reabsorption is effected by diffusion and is dependent upon sodium reabsorption. Primary active sodium reabsorption:

The essential feature underlying Na+ reabsorption throughout the tubule is the primary active transport of Na+ out of the cell and into the interstitial fluid. This transport is achieved by NaVK+ pumps in the basolateral membrane of the cells. The active transport of Na+ out of the cell keeps the intracellular concentration of Na+ low compared to the tubular lumen.

The present invention also relates to management of a patient's fluid, more specifically, providing an indication of "urine flow" such as an indication of renal perfusion, an indication of Glomerular Filtration Rate (GFR), changes in extracellular fluid, kidney function and urine irrigation problems, etc; and correlating the same with the measurement of electrolytes, oxygen content and other parameters, as described and claimed herein.

Since appropriate management of the fluid balance in the critically ill patient is essential, it is an object of the present invention to also provide a new diagnostic method that continuously monitors and measures urine output and urine flow and correlates the same to provide real time warning with regard to abnormal fluctuations.

In preferred embodiments of the present invention, the method utilizes a low flow metering device.

In especially preferred embodiments of the present invention the low flow metering device incorporates a drop generator and a droplet counter.

In a most preferred embodiment of the present invention, the present invention utilizes a modified version of the low flow metering device described and claimed in U.S. Pat. No. 6,640,649, the relevant teachings of which are incorporated herein by reference.

Preferably the method further comprises continuously monitoring and graphically representing, in real time, fluctuations in renal flow and renal output.

In especially preferred embodiments of the present invention the method further comprises providing alarm means.

The diagnostic method of the present invention allows for both the continuous monitoring and transmission of urine output and flow rate information together with information as to changes in a urinary parameter indicative of a body malfunction, as described herein, regarding a catheterized patient, to means which correlate and display the same in real time, and will be integrated into a system supplied to hospitals and other patient care facilities capable of showing an online and visual display of the urinary parameters.

Thus it will be realized that the method of the present invention provides the ICU and other medical facilities and departments with a valuable new diagnostic tool heretofore not available.

US 2006/0100743 to Townsend et al., teaches an automated non-invasive real-time acute renal failure detection system by real-time monitoring of urea and creatine. The system makes substantially continuous measurements of the urine flow rate and concentration of the analyte of interest. These may be monitored to detect if the patient experiences a delta change in the mass excretion rate of an analyte that is indicative of the onset of ARF or of a change in renal function.

Townsend et al. suggest on page 2 paragraph [0017], that "The absolute concentration of urine analytes are not generally clinically useful because of the large fluctuations in the amount of water dilution from sample to sample and person to person. Because of creatinine's steady excretion rate, it has been used as an internal standard to normalize the water variations."

Contrary to the teachings of Townsend et al, the present invention is directed to systems and methods for detecting body states using continuous urine monitoring of analytes, other than creatinine and urea. The systems and methods of the present invention also relate to the use of measurements of the analytes together with measurement of urine output and urine flow.

While the invention will now be described in connection with certain preferred embodiments in the following examples and with reference to the attached figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

BRIEF DESCRIPTION OF THE DRAWINGS

In order to understand the invention and to see how it may be carried out in practice, embodiments will now be described, by way of non-limiting example only, with reference to the accompanying drawings.

In the figures,

FIG. 1 D is a simplified schematic illustration of a LIX electrode incorporating the electrode tip of FIG. 1 B;

FIG. 1 E shows equipment for filling the electrode of FIG. 1 D with electrolyte;

FIG. 2 is a simplified flowchart of a method for continuous monitoring and detection of changes in parameter values and corrective actions to the changes according to some embodiments of the present invention;

FIG. 3 is a simplified flowchart of a method for continuous monitoring and detection of changes in urinary parameters and corrective actions to the trend changes according to some embodiments of the present invention;

FIG. 4 is table of typical findings in ARF and provides a diagnostic index relating to both prerenal and intrinsic renal findings.

FIG. 11 is a table showing various renal insults and disorders and treatments thereof;

FIGS. 12A and 12B show an electrode system according to at least some embodiments of the present invention, in which the electrodes are preferably oriented perpendicularly to the flow of urine.

DETAILED DESCRIPTION OF EXEMPLARY EMBODIMENTS

Figure 1A:
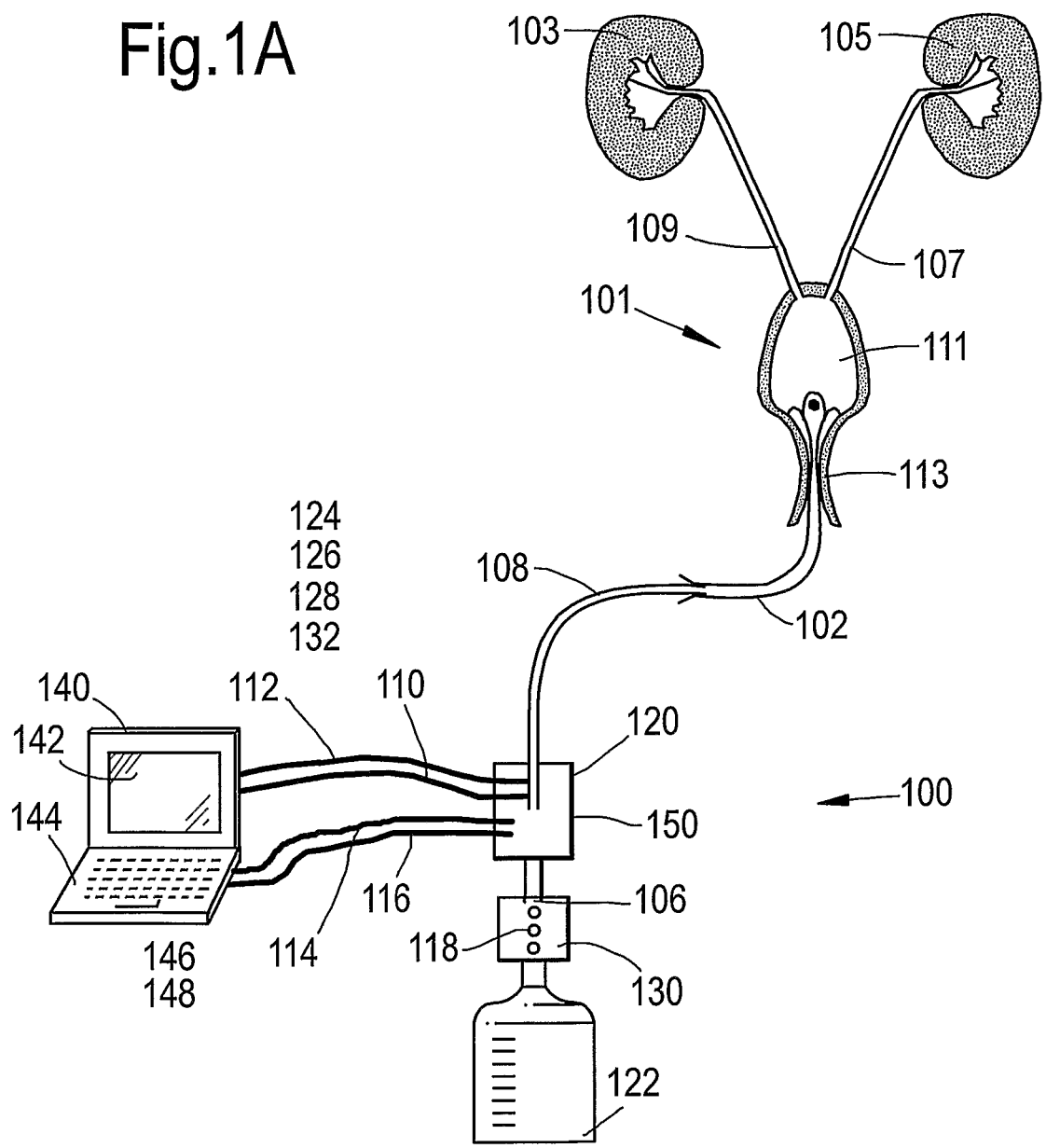
FIG. 1A is a simplified schematic illustration of a system for continuous monitoring and detection of a change in a body state according to some embodiments of the present invention.
Figure 1B:
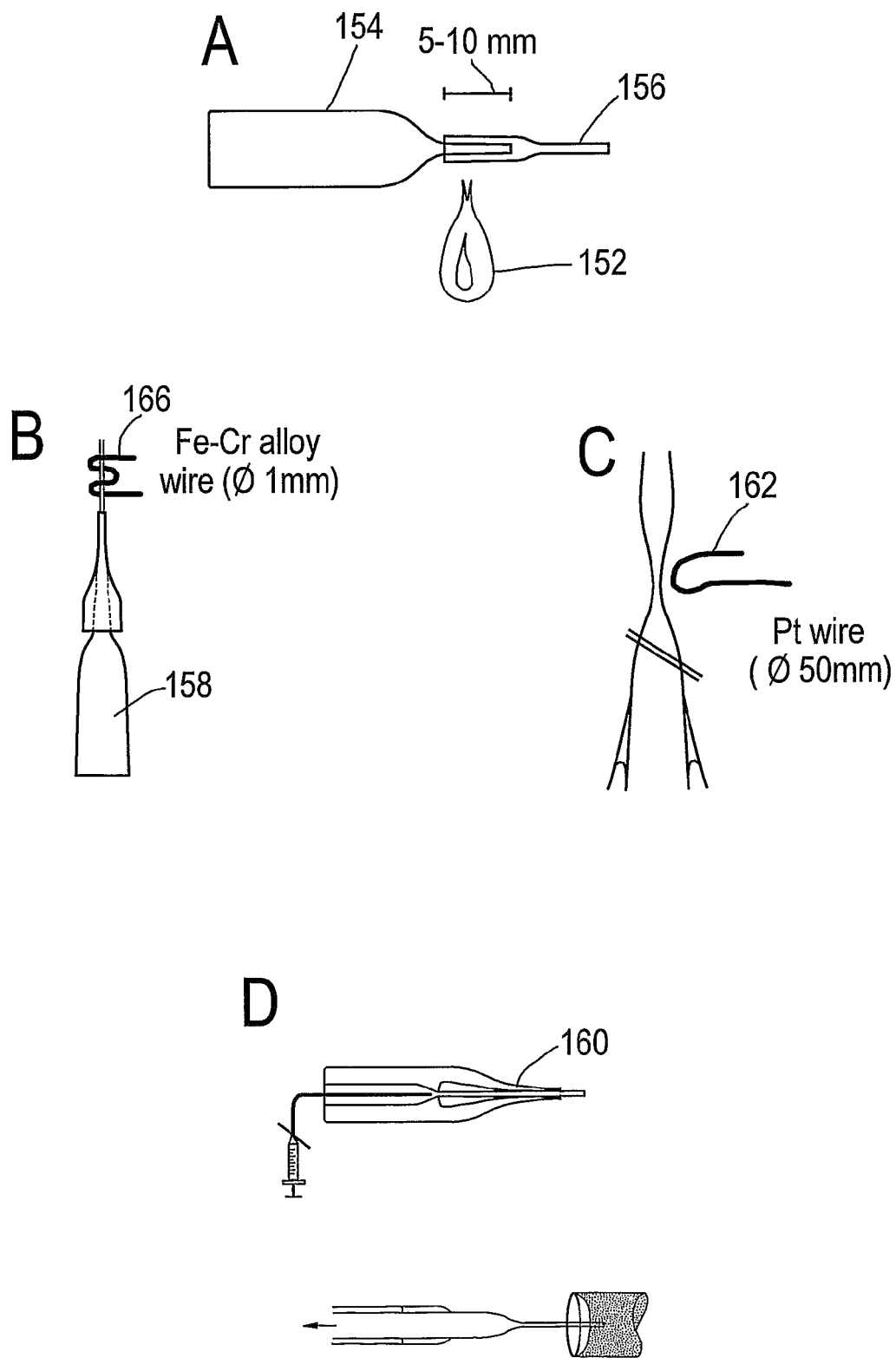
FIG. 1 B is a simplified schematic illustration of a method for preparing an electrode tip for an analyte detection apparatus in the system of FIG. 1A.
FIG. 1C is a simplified schematic image of a heating loop device for preparing an electrode tip of FIG. 1 B.
FIG. 1F shows an oxygen electrode of said analyte detection apparatus of FIG. 1 B.
Figure 1C:
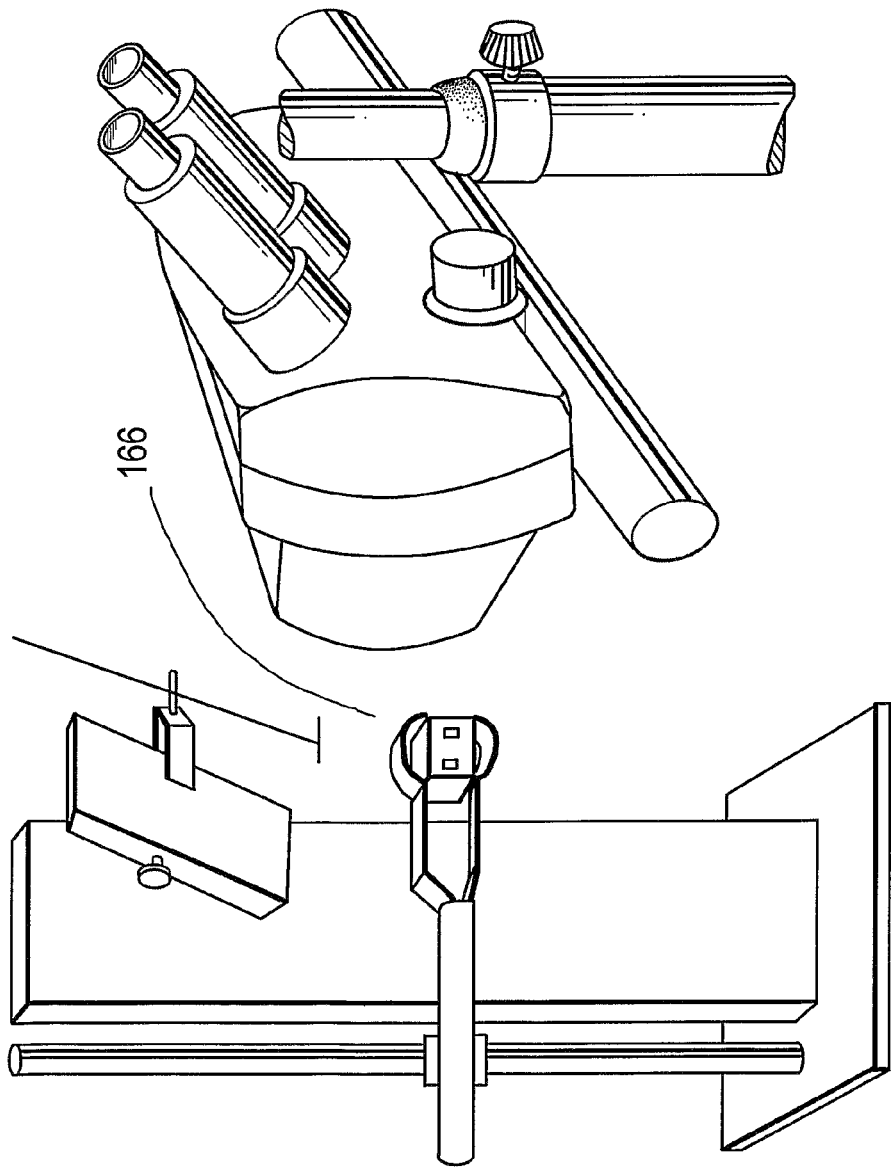
Figure 1E:
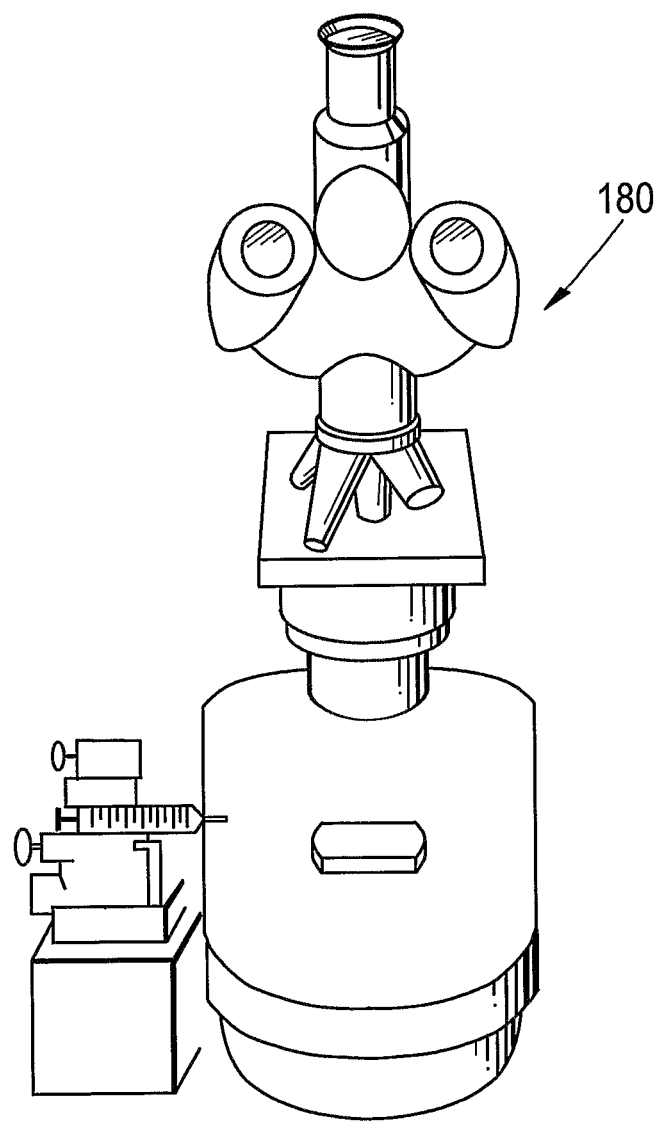

Reference is now made to FIG. 1A, which is a simplified schematic illustration of a system 100 for continuous monitoring and detection of a change in a body state according to some embodiments of the present invention.

A mammalian patient, such as a human 101, typically has two kidneys 103, 105 and two ureters 107, 109 for transportation of the urine from the kidneys to the bladder 111, and a urethra 113 for passage of the urine from the bladder for excretion out of the body.

System 100 comprises: a) a urine collection apparatus 120; b) a urine flow monitoring apparatus 130; c) a computer system 140; and d) analytes' monitoring system 150.

The urine collection apparatus 120 comprises a catheter 102 suitably connected through the urethra 113 into the bladder 111, as is known in the art. Apparatus 120 further comprises connection means 108 for connecting between the catheter 102 and a urine collection vessel 122 via urine flow monitoring apparatus 130 or analyzing device 150.

The urine flow monitoring apparatus 130 is typically connected between catheter 102 and connection means 108. Apparatus 130 typically comprises a low flow metering device 106.

In especially preferred embodiments of the present invention said low flow metering device incorporates a drop generator and a droplet counter.

In a most preferred embodiment of the present invention, the present invention utilizes a modified version of the low flow metering device described and claimed in U.S. Pat. No. 6,640,649, the relevant teachings of which are incorporated herein by reference.

Computer system 140 comprises a display 142, at least one inputting means 144, a memory 146 and a processing device 148.

The analyte monitoring system 150 comprises one or more electrodes 110, 112, 114, 116 for continuously monitoring corresponding one or more analytes.

According to some embodiments, the one or more electrodes are micro-, mini- or macro-sensors.

Electrodes 110, 112, 114, 116 are in communication with computer system 140 via unwired connections 124, 126, 128 and 132 respectively. According to some alternative embodiments, some or all of the connections may be wired connections.

The tips of the microelectrodes are immersed in the stream of urine in connection means 108. According to some additional or alternative embodiments, one or more electrodes may be placed in vessel 122.

Electrode 110, may be configured and operative to monitor, for example, a dissolved oxygen concentration, and a dissolved oxygen concentration change in the urine over time.

Electrode 112, may be configured and operative to monitor, for example, a sodium ion concentration, and a sodium ion concentration change in the urine over time.

Electrode 114, may be configured and operative to monitor, for example, a potassium ion concentration, and a potassium ion concentration change in the urine over time.

Electrode 116, may be configured and operative to monitor, for example, a pH and a pH change of the urine over time.

Many combinations of different electrodes and other devices for monitoring a large number of parameters of the urine are envisaged to be within the scope of the present invention. For example, the parameters being monitored in the urine may include, but are not limited to, one or more of the following: dissolved oxygen concentration; a dissolved oxygen concentration change over time; sodium ion concentration; a sodium ion concentration change over time; potassium ion concentration; a potassium ion concentration change; pH level; a pH level change over time; a bicarbonate concentration, a change in bicarbonate concentration over time; a carbonate concentration, a change in carbonate concentration over time; an osmolality; a change in osmolarity over time; a carbon dioxide concentration; a change in carbon dioxide concentration over time; a phosphate concentration; a change in phosphate concentration over time.

These electrodes are described in more detail with reference to FIGS. 1 B-1F hereinbelow.

According to some other embodiments, analytes' monitoring system 150 may comprise other monitoring means, such as a chromatographic device, a spectroscopic device or other devices (not shown) for on-line monitoring known in the art.

Computer system 140 is adapted to continuously monitor and graphically represent, in real time, concentrations, changes, trends and fluctuations in renal urine flow and renal urine output, as well as concentrations, changes, trends and fluctuations of any one or more of the parameters listed herein.

As was mentioned hereinabove, analytes' monitoring system 150 may comprise one or more micro sensors MICRO- MINI- OR MACRO-SENSORS General:

The sensor is a needle shaped device with a typical tip of several microns, which measures the concentration of a specific ion on compound (Gieske And De Beer, 2003). Micro sensors are powerful tools for the determination of local fluxes in microbial ecology (De Beer et al., 1997). The small dimensions of micro sensors allow the investigation of the chemical and physical microenvironment, as well as determining the rates of metabolic processes at high spatial resolution in our organisms.

Four different sensor types are available, based on amperometric, voltammetric, potentiometric and optical working principles. In this study we used amperometric and potentiometric micro sensors. Potentiometric sensors Potentiometric determinations are based on the measurement of an electrical potential difference across a selective membrane (De Beer et al., 2000). Three different types of membranes may be employed:

1. Full glass—the membrane consists of a pH sensitive glass similar to pH macro-electrode and/or an ion sensitive glass and/or any other material;
2. Metal oxide—iridium oxide pH sensor, which is not applied to environmental samples yet; and
3. Electrodes that are based on a liquid ion-exchanging membrane (LIX). Cell physiologists for intracellular measurements of various ion concentrations developed the LIX sensors technique. The principle of LIX sensors is the measurements of the electrical potential difference that develops over an ion selective membrane.

An ideal ion selective membrane is sensitive to one type of ion. The difference of the electrical potentials ($\Delta E$) between the two interfaces is according to Nernst equation:

wherein R is the gas constant, T the absolute temperature, z the charge number of the ion, F the faraday constant and a,- and ae the ion activity in the sample, and filling electrolyte solution. The activity in the filling electrolyte a-, can be considered as constant, therefore:

RT $\Delta E = E0 + \ln OJ$ Or $\Delta E = E0 + K^* \log(\alpha)$ zF where E0 is the offset potential, K is the slope factor amounting 59.2/z mV at 25° C. Usually in micro-sensors Nernst-like behavior is not observed due to different deviations.

LIX micro sensors consist of a glass with an ion exchanging lipophilic liquid in the tip acting as functional membrane. Potentiometric micro sensors function the same way as macro sensors. The LIX is positioned in a capillary tip and the solvents used for its membrane are hydrophobic. To prevent displacement of the LIX by water, the inner surface of the micro sensors are rendered hydrophobic by silanization (Amman, 1986; Thomas, 1978). To avoid noises a liquid coaxial shielding can be made around the sensor (Boudreau and Jorgensen, 2001). In our laboratory we shield with 3 M KCI. With such a coaxial shielding, noise pickup is negligible and the signal can be read at 0.01 mV accuracy. The high accuracy helps to determine small fluxes of some ions, such as, but not limited to, $Ca^{2+}$.

FIG. 1 B refers to the depiction of the preparation of the fine tip. Procedure for LIX micro-sensor preparation:

1. Pulling of glass capillaries (FIG. 1 B): a. Green glass 154 is heated by a flame 152 of a Bunsen burner and pulled to 1 mm thickness. b. White glass 158 is heated and pulled to 2 mm thickness. c. The white glass and the green glass are fused together under the flame. d. A tip 160 is produced under the microscope with a thin platinum-heating loop 162 (FIG. 1 B).
2. Silanization of the glass capillaries: The silanization reduces the leaking of ionophores from the glass. The procedure must be performed in a fume hood.

The capillaries 166, which were made, are placed in a sealed glass container at a temperature of 200° C. N,N-dimethyltrimethylsilylamine is added to the sealed container for 24 hours.

3. Sensor shielding (FIG. 1D): The shielding of the capillaries is made with Pasteur pipettes 170. The pasture pipette is glued to the electrode 1-2 cm above tip 160. The shield liquid 176 is 3 M KCI that exists between the Pasteur pipette and the capillaries.
4. mV meter: For potentiometeric measurements the milivoltmeter used as it has a high impedance input of 1015 mV. The milivoltmeters used in our laboratory are made by Mascom, Germany, as well as one that is a self-made milivoltmeter configured according to the Mascom design. pH sensors:

LIX type sensors for H+ have been used extensively for physiological purposes and are characterized by a very high selectivity (Boudreau and Jorgensen, 2001). In our field, two types of liquid ion exchange membranes are used: Type 1 H+ Ionophore II, ETH 1907), has a measuring range of between pH 2-9.5; and Type 2 (H+ Ionophore III), which has a measuring range of between pH 3-11 (De Beer et al., 1997). In recent research, the second type was preferred due to its wide pH range. $Ca^{2+}$ sensors:

LIX type micro sensor for $Ca^{2+}$ is used in biomedical and physiology studies. Due to the excellent performance of the $Ca^{2+}$ LIX available, it is also possible to analyze $Ca^{2+}$ in seawater and fresh water (Boudreau and Jorgensen, 2001). The liquid ion exchange is ($Ca^{2+}$ Il ionophore).

$CO_3^{2'}$ Sensors:

The $CO_3^{2'}$ microsensor is a new development. The LIX has been taken from Choi et al., (2002), and miniaturized for use with the microsensor method. The Calibration is made in a closed chamber using seawater whose pH was modified from 9.1 to a pH of 7.6 as the modification changes the $CO_3^{2"}$ concentration. A Nernst behavior was observed. The selectivity of this micro-sensor is now being investigated (more details will discussed in the section relating to $CO_3^{2"}$). Na+ sensor The Na+ sensor is built using a liquid ion exchanger of Fluka and is constructed from sensitive glass for Na+. Amperometric microelectrodes:

The measurements are based on currents induced by the electrochemical reduction or oxidation of the substrate in the tip, with a rate proportional to its concentration. Sensors based on the principle above are used for: $O_2$, $N_2O$, $H_2S$ and HCIO. The $O_2$ electrode is the most used type and has been applied by many research groups to study photosynthesis and respiration in various systems (Gieske And De Beer, 2003). $O_2$ electrodes The $O_2$ electrodes are Clark-type sensors with a gold-coated cathode situated behind a silicon membrane and immersed in an electrolyte solution. The measuring principle is based on the rate of reduction of $O_2$, which is diffused through the silicone membrane to the cathode (with 0.8V). The oxygen sensor is very stable and is without background noise due to the guard cathode which prevents diffusion of $O_2$ from behind to the measuring cathode (Revsbech, 1989). Manufacturing of $O_2$ electrodes: 1. Cathode: FIG. 1F A cathode 184 is made from a 5 cm piece of 50-μm thick platinum wires. This is first etched in saturated KCN with 2 V AC applied between the platinum wire and a graphite rod, to a tip size of 1 μm.

The platinum wire should be inserted into the green glass 154 under the Bunsen burner. The green glass is fused with the white glass 158. Later the platinum wire is fused to the green glass in the heating loop (FIG. 1 E). The exposure of the platinum wire from the green glass is effected with a small heating loop. The exposed platinum wire must be approximately 10 μm.

The cathode is coated with gold by electroplating to form a gold tip 186. The gold solution is prepared in a Pasteur pipette. Working under a microscope, the platinum cathode is brought into the field of vision. A potential of −0.6 V of gold solution is applied to the tip until the tip is coated with a gold crusted sphere having a diameter of 5-10 μm.

Casing

The outer casing of the electrode is made from a Pasteur pipette 166. The pipette is first pulled in flame, then under a heating loop. The tip is sealed with a silicon membrane 178 of approximately 10 μm.

Guard Cathode

A guard cathode 188 is made by etching a silver wire in saturated KCN1 the wire is then positioned in a glass and sealed with glue or with a heating loop.

Reference

A reference anode 172 is made from a 100 μm thick chlorinated silver wire.

Connection and Calibration

The sensor is connected to a picoampmeter. The potential on the gold cathode and the guard is −0.075 V relative to the reference electrode. At this potential, O2 will be reduced: $0.5 O_2 + 2e^- + H^+ \rightarrow OH^-$.

The guard cathode with a large surface will consume all of the O2 in electrolyte 176. Only the O2 diffusing through the silicon membrane 178 at the tip will reach the gold tip 186 of the main cathode. The current through the gold cathode is linearly proportional to the O2 concentration near the tip of the sensor. The current between the gold cathode and the reference is measured with the picoampmeter. The order of the sequenced connection procedure of the sensor to the picoampmeter is very important: first the reference is connected, then the guard cathode and finally the main gold cathode. Any other sequence used to connect the sensor to the picoampmeter will cause the formation of gas bubbles in the tip, which will harm the electrode. After the connection is made, the sensor must be placed in saturated water for several hours until stabilization is achieved. Since the signal with O2 concentration is linear, a two point calibration in saturated air and N2 should be enough. Micro-sensors:

As will now be explained, Na+, K+ and O2 are key parameters for monitoring kidney and homodynamic body functions.

Both sodium and water freely filtrate from the glomerular capillaries into bowman's space because they have low molecular weights and circulate in the plasma as a free form. The Na+ and water undergo considerable reabsorption, normally more than 99%, but no secretion. Most renal energy utilization goes to accomplish this enormous reabsorptive task. The bulk water and Na+ reabsorption (about two thirds) occurs in the proximal tubule, but the major hormonal control of reabsorption is exerted on the distal convoluted tubules and collecting duct.

The Na+ reabsorption is an active process occurring in all tubular segments except the descending limb of the loop of Henle, and water reabsorption is by diffusion and is dependent upon sodium reabsorption.

Since Na+ is freely filterable from the glomerular capillaries into Bowman's space and actively reabsorbed but not secreted, the amount of sodium excreted in the urine represents the result of two processes: sodium filtration—sodium reabsorption. Clinical changes in urinary concentrating ability Of clinical importance is the fact that inability to achieve maximal urinary concentration occurs early in any renal disease because of interference with the establishment of the medullary gradient. Any significant change in renal structure, particularly in the medulla, can upset the intricate geometric relationships required for maximal countercurrent functioning. A change in renal blood flow to the medulla, either too much or too little, will reduce the gradient by carrying away too much or too little water and/or solutes. Destruction of the loops will also reduce the gradient as will decrease Na+ and Cl" pumping by the ascending limb. The latter may be caused by tubular disease or by a marked reduction in GFR and thereby, a reduction in the supply of Na+ and CT to the loop. Another important factor is flow rate through the loop. Any large increase washes out the gradient, thereby preventing concentration of the final urine.

With the electrode technique of measuring Na+, K+, Cl" and O2 we will be able to detect any early changes in the concentrating mechanism of henle loop.

In normal persons, urinary Na+ excretion is reflexly increased when there is a Na+ excess in the body and reflexly decreased when there is Na+ deficit. Theses reflexes are so precise that total body Na+ normally varies by only a small percentage despite a wide range of Na+ intakes and the sporadic occurrence of large losses via the skin or gastrointestinal tract. Since Na+ is freely filterable at the renal corpuscle and reabsorbed but not secreted the amount of Na+ is the sum of these two processes. Abnormal Na+ retention:

In several types of diseases, Na+ balance become deranged by the failure of the kidneys to excrete Na+ normally. Sodium excretion may fall virtually to zero and remain there despite continued Na+ ingestion. The person retains large quantities of Na+ and water, leading to the abnormal expansion of extracellular fluid and formation of edema.

Acute Renal Failure (ARF)

Acute renal failure (ARF) is a syndrome characterized by rapid decline in glomerular filtration rate (hours to days), retention of nitrogenous waste products, and perturbation of extracellular fluid volume and electrolyte and acid-base homeostasis. ARF occurs in approximately 5% of hospital admissions and up to 30% of admissions to intensive care units. Oliguria (urine output>400 ml_/d) is a frequent but not invariable clinical feature (50%). ARF is usually asymptomatic and diagnosed when biochemical monitoring of hospitalized patients reveals a recent increase in blood urea and creatinine concentrations. It may complicate a wide range of diseases, which for purposes of diagnosis and management are conveniently divided into three categories: (1) diseases that cause renal hypoperfusion without compromising the integrity of renal parenchyma {prerenal ARF, prerenal azotemia) (55%); (2) diseases that directly involve renal parenchyma (intrinsic renal ARF, renal azotemia) (40%); and (3) diseases associated with urinary tract obstruction (postrenal ARF, postrenal azotemia) (5%). Most ARF is reversible, the kidney being relatively unique among major organs in its ability to recover from almost complete loss of function. Nevertheless, ARF is associated with major in-hospital morbidity and mortality, in large part due to the serious nature of the illnesses that precipitate the ARF.

Prerenal Arf (Prerenal Azotemia)

Prerenal ARF is the most common form of ARF and represents a physiologic response to mild to moderate renal hypoperfusion. Prerenal ARF is by definition rapidly reversible upon restoration of renal blood flow and glomerular ultrafiltration pressure. Renal parenchymal tissue is not damaged; indeed, kidneys from individuals with prerenal ARF function well when transplanted into recipients with normal cardiovascular function. More severe hypoperfusion may lead to ischemic injury of renal parenchyma and intrinsic renal ARF. Thus, prerenal ARF and intrinsic renal ARF due to ischemia are part of a spectrum of manifestations of renal hypoperfusion. Prerenal ARF can complicate any disease that induces hypovolemia, low cardiac output, systemic vasodilatation, or selective intrarenal vasoconstriction. Hypovolemia leads to a fall in mean systemic arterial pressure, which is detected as reduced stretch by arterial (e.g., carotid sinus) and cardiac baroreceptors. Activated baroreceptors trigger a coordinated series of neural and humoral responses designed to restore blood volume and arterial pressure. These include activation of the sympathetic nervous system and renin-angiotensin-aldosterone system and release of arginine vasopressin (AVP; formerly called antidiuretic hormone). Norepinephrine, angiotensin II, and AVP act in concert in an attempt to preserve cardiac and cerebral perfusion by stimulating vasoconstriction in relatively "nonessential" vascular beds, such as the musculocutaneous and splanchnic circulations, by inhibiting salt loss through sweat glands, by stimulating thirst and salt appetite, and by promoting renal salt and water retention. Glomerular perfusion, ultra-filtration pressure, and filtration rate are preserved during mild hypoperfusion through several compensatory mechanisms. Stretch receptors in afferent arterioles, in response to a reduction in perfusion pressure, trigger afferent arteriolar vasodilatation through a local myogenic reflex (autoregulation). Biosynthesis of vasodilator prostaglandins (e.g., prostaglandin E2 and prostacyclin) is also enhanced, and these compounds preferentially dilate afferent arterioles. In addition, angiotensin Il induces preferential constriction of efferent arterioles. As a result, intraglomerular pressure is maintained, the fraction of plasma flowing through glomerular capillaries that is filtered is increased (filtration fraction), and glomerular filtration rate (GFR) is preserved. During states of more severe hypoperfusion, these compensatory responses are overwhelmed and GFR falls, leading to prerenal ARF. Autoregulatory dilatation of afferent arterioles is maximal at mean systemic arterial blood pressures of 80 mmHg, and hypotension below this level is associated with a precipitous decline in GFR. Lesser degrees of hypotension may provoke prerenal ARF in the elderly and in patients with diseases affecting the integrity of afferent arterioles (e.g., hypertensive nephrosclerosis, diabetic vasculopathy).

Hepatorenal Syndrome

This is a particularly aggressive form of ARF, with many of the features of prerenal ARF, that frequently complicates hepatic failure due to advanced cirrhosis or other liver diseases, including malignancy, hepatic resection, and biliary obstruction. In fullblown hepatorenal syndrome, ARF progresses even after optimization.

Intrinsic Renal Arf (Intrinsic Renal Azotemia)

Intrinsic renal ARF can complicate many diverse diseases of the renal parenchyma. From a clinicopathologic viewpoint, it is useful to divide the causes of intrinsic renal ARF into (1) diseases of larger renal vessels, (2) diseases of the renal microcirculation and glomeruli, (3) ischemic and nephrotoxic ARF, and (4) tubulointerstitial inflammation. Most intrinsic renal ARF is triggered by ischemia (ischemic ARF) or nephrotoxins (nephrotoxic ARF), insults that classically induce acute tubular necrosis (ATN). Accordingly, the terms ARF and ATN are usually used interchangeably in these settings. However, as many as 20 to 30% of patients with ischemic or nephrotoxic ARF do not have clinical (granular or tubular cell urinary casts) or morphologic evidence of tubular necrosis, underscoring the role of sublethal injury to tubular epithelium and injury to other renal cells (e.g., endothelial cells) in the pathophysiology of this syndrome. Etiology and Pathophysiology of Ischemic ARF Prerenal ARF and ischemic ARF are part of a spectrum of manifestations of renal hypoperfusion. Ischemic ARF differs from prerenal ARF in that the hypoperfusion induces ischemic injury to renal parenchymal cells, particularly tubular epithelium, and recovery typically takes 1 to 2 weeks after normalization of renal perfusion as it requires repair and regeneration of renal cells. In its most extreme form, ischemia leads to bilateral renal cortical necrosis and irreversible renal failure. Ischemic ARF occurs most frequently in patients undergoing major cardiovascular surgery or suffering severe trauma, hemorrhage, sepsis, and/or volume depletion. Ischemic ARF can also complicate milder forms of true hypovolemia or reduced "effective" arterial blood volume if they occur in the presence of other insults (e.g., nephrotoxins or sepsis) or in patients with compromised autoregulatory defense mechanisms or preexisting renal disease. The course of ischemic ARF is typically characterized by three phases: the initiation, maintenance, and recovery phases. The initiation phase (hours to days) is the initial period of renal hypoperfusion during which ischemic injury is evolving. GFR declines because (1) glomerular ultrafiltration pressure is reduced as a consequence of the fall in renal blood flow, (2) the flow of glomerular filtrate within tubules is obstructed by casts comprised of epithelial cells and necrotic debris derived from ischemic tubule epithelium, and (3) there is backleak of glomerular filtrate through injured tubular epithelium. Ischemic injury is most prominent in the terminal medullary portion of the proximal tubule (S3 segment, pars recta) and the medullary portion of the thick ascending limb of the loop of Henle. Both segments have high rates of active (ATP-dependent) solute transport and oxygen consumption and are located in a zone of the kidney (the outer medulla) that is relatively ischemic, even under basal conditions, by virtue of the unique countercurrent arrangement of the medullary vasculature.

Cellular ischemia results in a series of alterations in energetics, ion transport, and membrane integrity that ultimately lead to cell injury and, if severe, cell apoptosis or necrosis. These alterations include depletion of ATP, inhibition of active sodium transport and transport of other solutes, impairment of cell volume regulation and cell swelling, cytoskeletal disruption and loss of cell polarity, cell-cell and cellmatrix attachment, accumulation of intracellular calcium, altered phospholipid metabolism, oxygen free radical formation, and peroxidation of membrane lipids. Importantly, renal injury can be limited by restoration of renal blood flow during this period.

The initiation phase is followed by a maintenance phase (typically 1 to 2 weeks) during which renal cell injury is established, GFR stabilizes at its nadir (typically 5 to 10 mL/min), urine output is lowest, and uremic complications arise (see below). The reasons why the GFR remains low during this phase, despite correction of systemic hemodynamics, are still being defined. Putative mechanisms include persistent intrarenal vasoconstriction and medullary ischemia triggered by dysregulated release of vasoactive mediators from injured endothelial cells (e.g., decreased nitric oxide, increased endothelin-1, adenosine, and platelet-activating factor), congestion of medullary blood vessels, and reperfusion injury induced by reactive oxygen species and other mediators derived from leukocytes or renal parenchymal cells.

The table seen in FIG. 4 presents typical findings in ARF which can be correlated with sodium measurements of the present invention.

The Use of Na+, K+ and O2 Electrodes

ARF impairs renal excretion of sodium, potassium, and water and perturbs divalent cation homeostasis and urinary acidification mechanisms. As a result, ARF is frequently complicated by intravascular volume overload, hyponatremia, hyperkalemia, hyperphosphatemia, hypocalcemia, hypermagnesemia, and metabolic acidosis.

Figure 5:
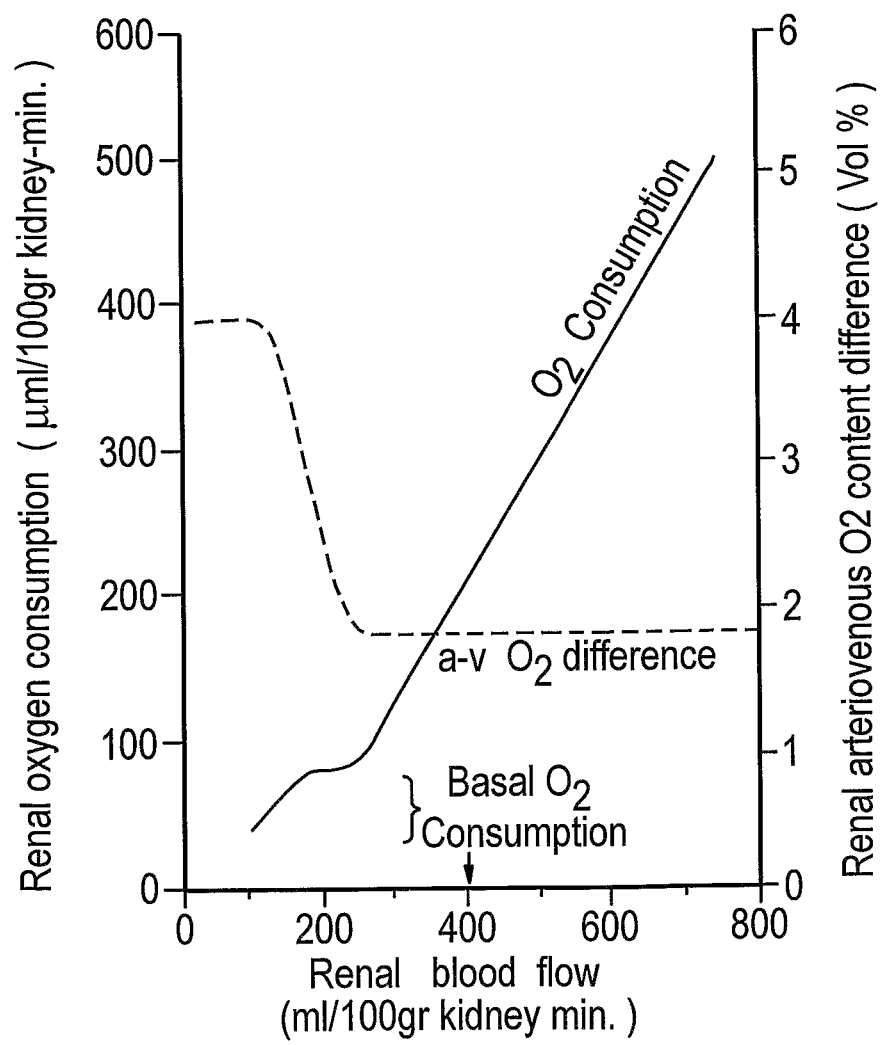
FIG. 5 is a graph showing the correlation of renal oxygen consumption, renal blood flow, renal arteriovenous O2 content difference, and basal O2 consumption.
Figure 6:
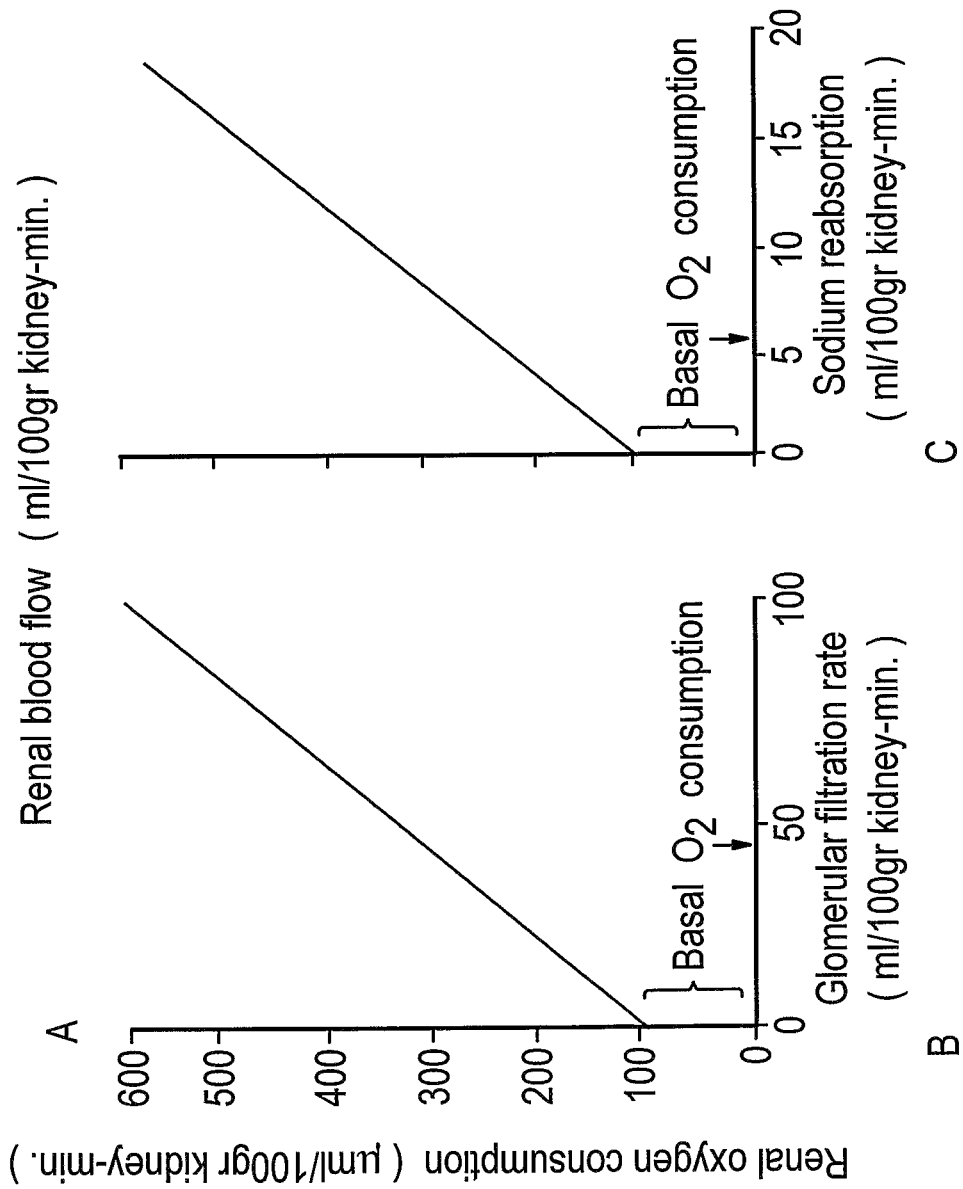
FIGS. 6A-6C are graphs showing the correlation of renal oxygen consumption, renal blood flow, basal O2 consumption, glomerular filtration rate and sodium reabsorption.
Figure 7:
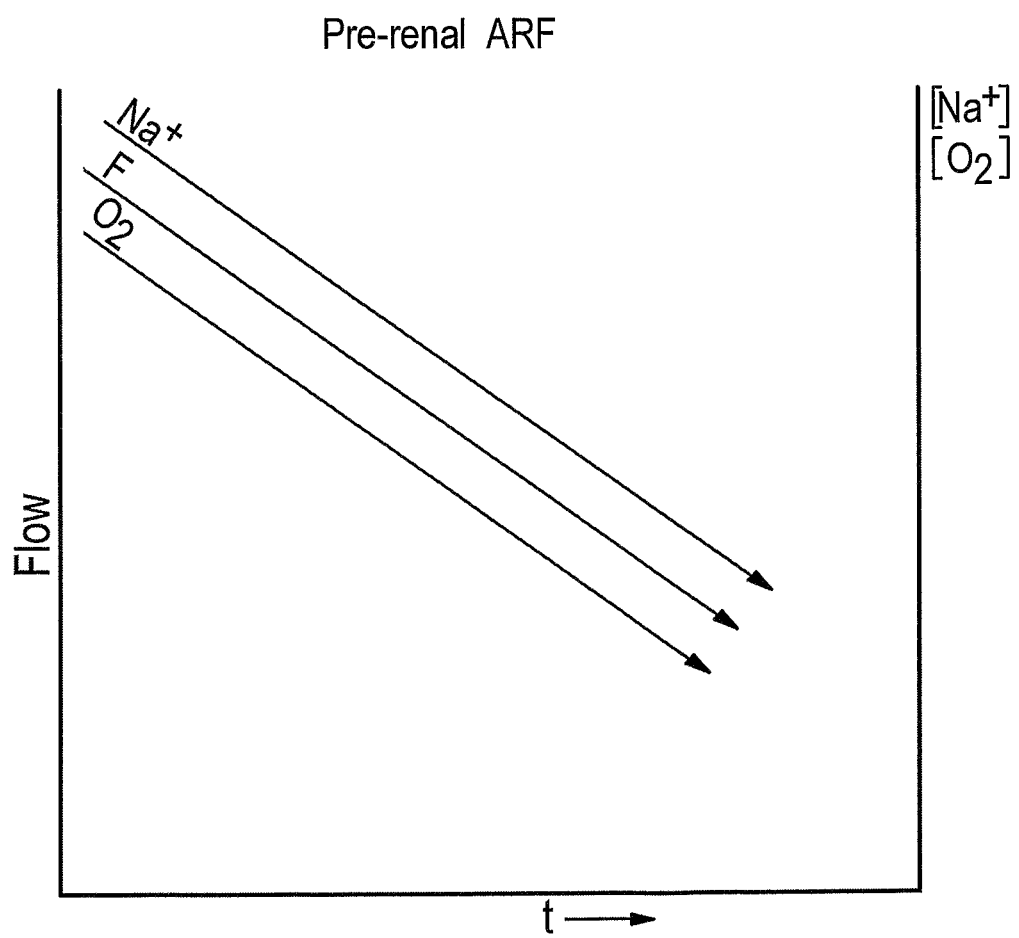
FIG. 7 is a graph showing the correlation of continuous urine flow and time with sodium and oxygen content as an indicator of prerenal ARF.
Figure 8:
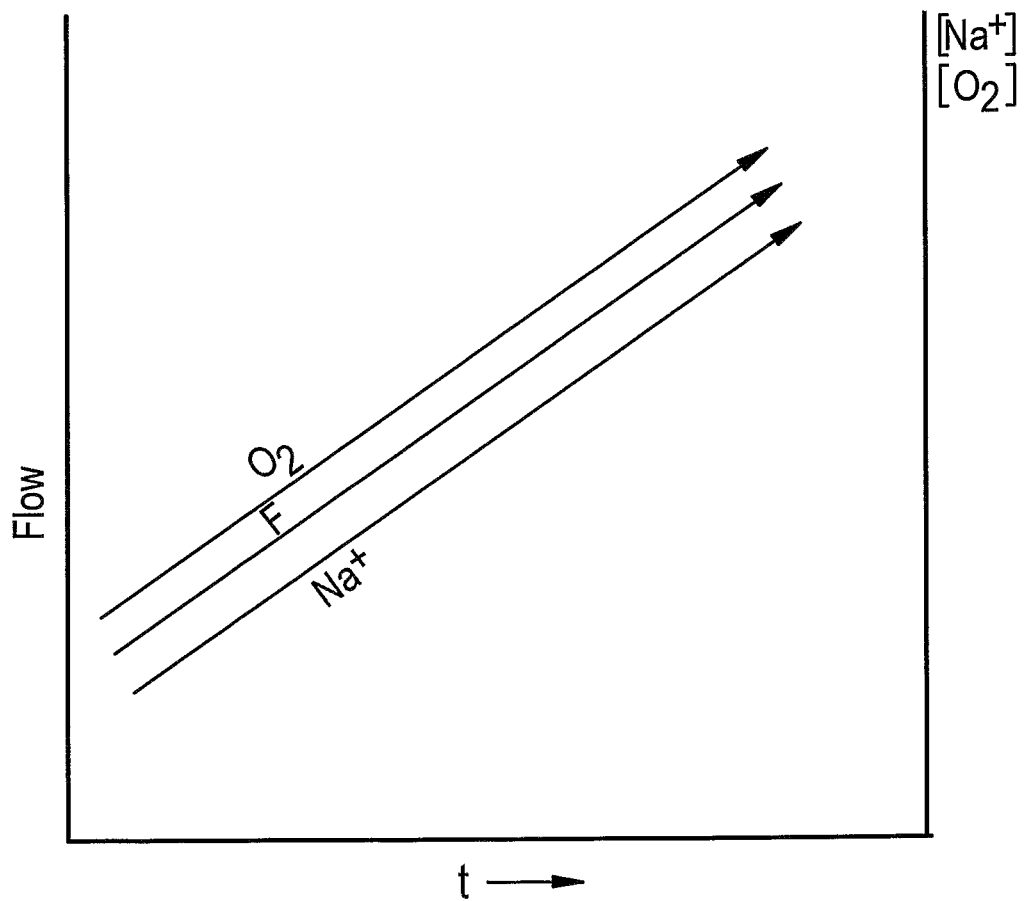
FIG. 8 is a graph showing the correlation of flow and time with sodium and oxygen content as an indicator of acute tubular narcrosis.
Figure 9:
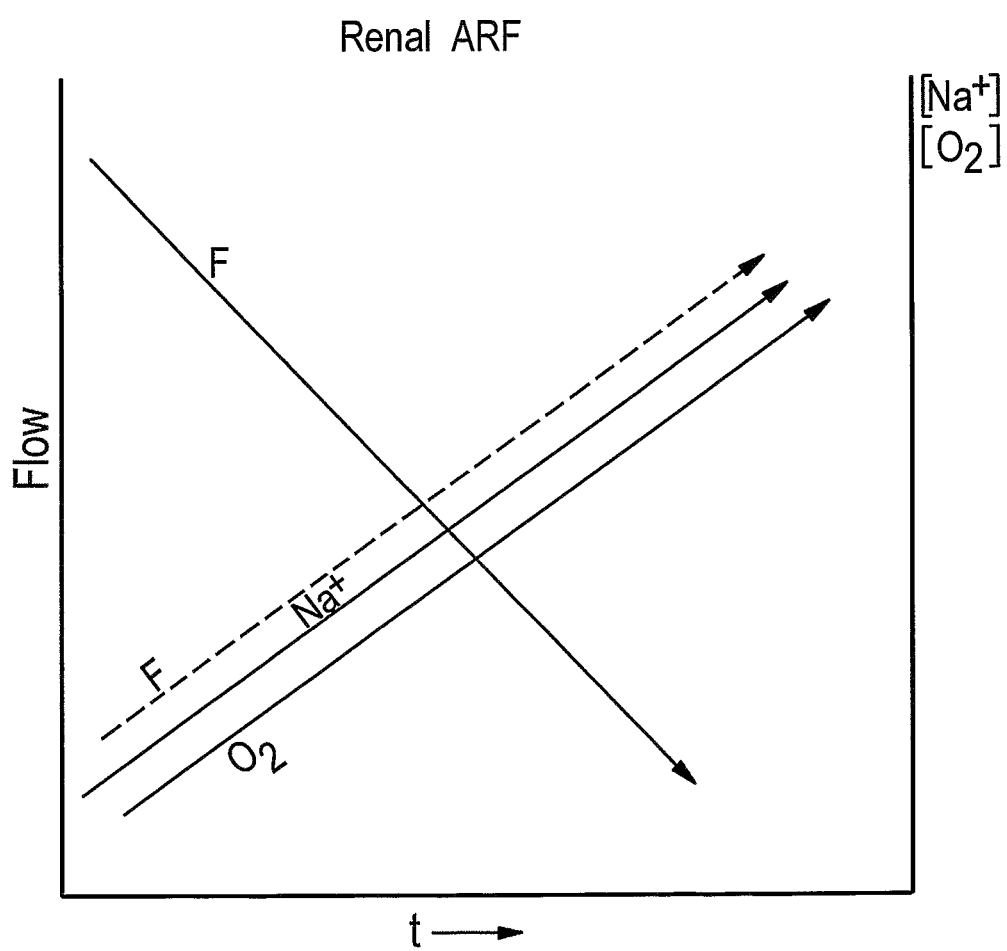
FIG. 9 is a graph showing the correlation of flow and time with sodium and oxygen content as an indicator of renal ARF.
Figure 10:
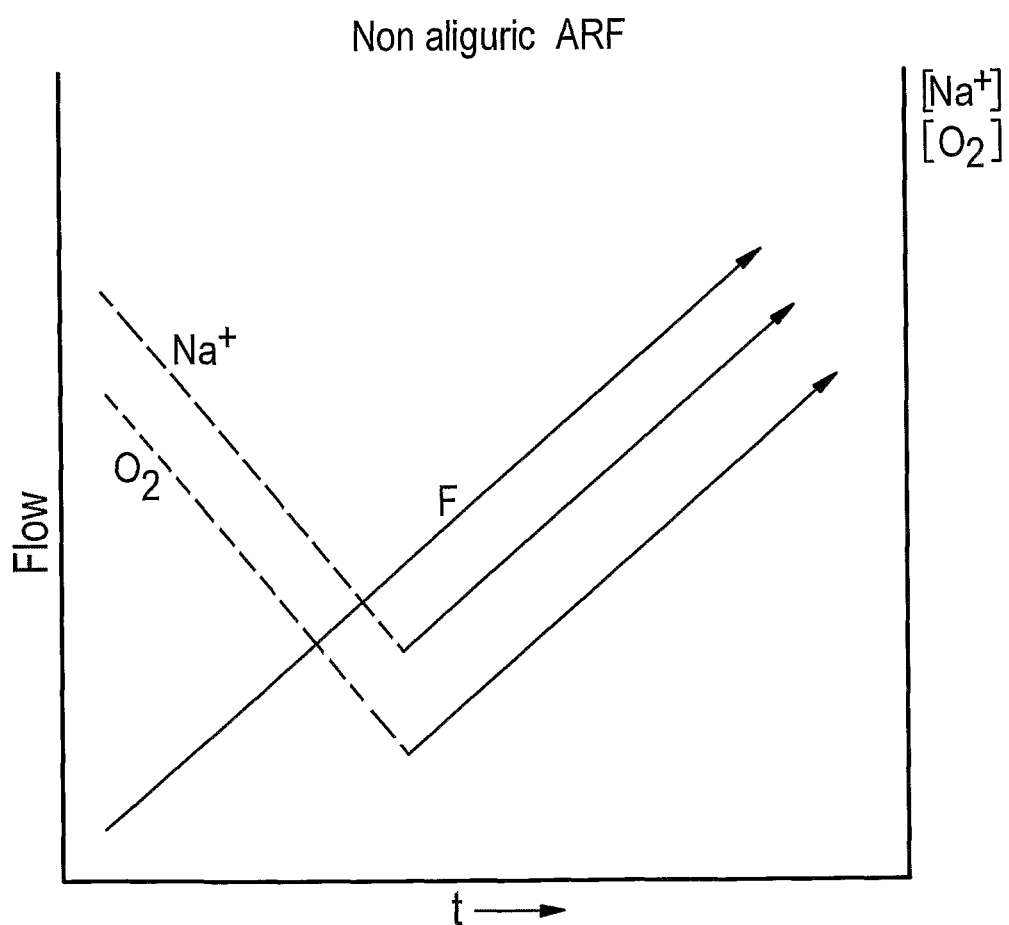
FIG. 10 is a graph showing the correlation of flow and time with sodium and oxygen content as an indicator of non-aliguric ARF.

By measuring online the Na+, K+ and the O2 it is possible to detect and thus prevent the diseases above. O2 measurements with Na+ and flow With the unique technique of measuring O2 according to the present invention, it is possible to correlate the O2 measurements to renal blood flow, GFR and sodium reabsorption as seen in FIGS. 5 and 6 appended hereto.

It is also possible to detect the dissolved oxygen in the urine with the flow and correlate it with GFR and with Na+ reabsorption. By measuring oxygen it is possible to detect and identify renal ischemia, since the oxygen is freely moving in the renal system the lack of oxygen in the renal system with high Na+ in the urine can indicate renal dysfunction; moreover in acute tubular necrosis it is possible to measure very high concentrations of O2 and very high concentration of Na+ as well. Na+ and flow As seen with relation to FIGS. 7-10, by measuring Na+, oxygen content and urine flow, it is possible to distinguish between pre-renal ARF, acute tubular narcrosis, intrinsic renal ARF, and non-aliguric ARF in that low flow of urine with high content of Na+ can imply on intrinsic renal ARF. Low Na+ with low flow can imply on pre-renal problems. All of them together with the oxygen will help to define and thus treat better the pathophysiological problems concerning to kidney dysfunction. Osmolarity Osmolarity is the sum of the electrolytes in the urine. By measuring Na+, K+ as the major electrolytes, it is possible to define with good accuracy the osmolarity of the urine online. Conductivity Conductivity is the measurement of the ability of a solution to carry an electrical current. The conductivity of a solution that has more dissolved ions will be higher, and thus measurements of Na+ and K+ as the main ions in the urine can be measured with conductivity measurements as well. pH measurements The pH of extracellular fluid is normally maintained within a narrow range (7.36 to 7.44) despite day-today fluctuations in the quantity of acids added to the extracellular fluid from dietary and metabolic sources (approximately 1 mmol H per kilogram of body weight per day). These acids consume buffers from both extracellular and intracellular fluid, of which HCO3 is the most important in the intracellular compartment. Such buffering minimizes changes in pH. Long-term effectiveness of the HCO3 buffer system, however, requires mechanisms for replenishment, otherwise unrelenting acquisition of nonvolatile acids from dietary and metabolic sources would ultimately exhaust buffering capacity, culminating in fatal acidosis. The kidneys normally function to prevent this eventuality by regenerating bicarbonate, thereby maintaining plasma concentrations of HCO3. In addition, the kidneys also reclaim HCO3 in the glomerular ultrafiltrate. The reabsorption of filtered HCO3 occurs by the following mechanism.

Filtered bicarbonate combines with H+ secreted from proximal tubule cells via the NaVH+ exchange, to form carbonic acid (H2CO3). Dehydration of carbonic acid under the influence of luminal carbonic anhydrase yields H2O and CO2, which is free to diffuse from lumen to peritubular blood. In the proximal tubule cell, the OH' left behind by the H+ secretion reacts with CO2, under the influence of intracellular carbonic anhydrase, forming HCO3 This ion is transported across the contraluminal proximal tubule cell membrane, via an electrogenic Na/HCO3 cotransporter, to reenter the extracellular HCO3 pool. The net result is reclamation of a filtered bicarbonate ion. Hydrogen ions in the urine are bound to filtered buffers (e.g., phosphate) in amounts equivalent to the amounts of alkali required to titrate the pH of the urine up to the pH of the blood (the so-called titratable acid). It is not usually possible to excrete all the daily acid load in the form of titratable acid due to limits of urinary pH. Metabolism of glutamine by proximal tubule cells to yield ammonium (ammoniagenesis) serves as an additional mechanism for H+ elimination and bicarbonate regeneration. Glutamine metabolism forms not only NH4 (i.e., NH3 plus H+) but also HCO3 which is transported across the proximal tubule (HCO3 regeneration). The NH4 must be excreted in the urine for this process to be effective in bicarbonate regeneration. Ammoniagenesis is responsive to the acid-base needs of the individual. When faced with an acute acid burden and an increased need for HCO3 regeneration, the rate of renal ammonia synthesis increases sharply. The quantity of hydrogen ions excreted as titratable acid and NH4 is equal to the quantity of HCO3 regenerated in tubule cells and added to plasma. Under steady-state conditions, the net quantity of acid excreted into the urine (the sum of titratable acid and NH4 less HCO3 must equal the quantity of acid gained by the extracellular fluid from all sources. Metabolic acidosis and alkalosis result when this delicate balance is perturbed, the former the result of insufficient net acid excretion, and the latter due to excessive acid excretion. Progressive loss of renal function usually causes little or no change in arterial pH, plasma bicarbonate concentration, or arterial carbon dioxide tension (PCO) until GFR falls below 25% of normal. Thereafter, all three tend to decline as metabolic acidosis ensues. In general, the metabolic acidosis of CRF is not due to overproduction of acids but is rather a reflection of nephron loss, which limits the amount of NH3 (and therefore also HCO3) that can be generated. Although surviving nephrons appear to be capable of generating supranormal amounts of NH3 per nephron, the diminished nephron population causes overall production to be reduced to an extent that is insufficient to permit adequate buffering of H in urine. As a result, although patients with CRF may be able to acidify their urine normally (i.e., urine pH as low as 4.5), the defect in NH3 production limits daily net acid excretion to 30 to 40 mmol, or one-half to two-thirds the quantity of nonvolatile acid added to the extracellular fluid in the same time period. Metabolic acidosis resulting from this daily positive balance of H is seldom florid in CRF of mild to moderate severity. Relative stability of plasma bicarbonate (albeit at reduced levels of 14 to 18 mmol/L) is maintained at the expense of buffering by bone. Because it contains large reserves of alkaline salts (calcium phosphate and calcium bicarbonate), bone constitutes a major reserve of buffering capacity. Dissolution of these buffers contributes to the osteodystrophy of CRF. Although the acidosis of CRF is due to loss of tubule mass, it nevertheless depends to a large part on the level of GFR. When GFR is reduced to only a moderate extent (i.e., to about 50% of normal), retention of anions, principally sulfates and phosphates, is not pronounced. Therefore, as the plasma HCO3 falls owing to dysfunction or loss of tubules, retention of Cl" by the kidneys leads to a hyperchloremic acidosis. At this stage the anion gap is normal. With further reductions in GFR and progressive azotemia, however, the retention of phosphates, sulfates, and other unmeasured anions ensues and plasma Cl falls to normal levels despite the reduction in plasma HCO3 concentration. An elevated anion gap therefore develops.

By measuring Na+, K+' O2 and pH it is possible to identify and detect most of the renal insults and dysfunctions as described in the table in FIG. 11 appended hereto, and to treat and/or reverse the same by known methods as listed in said table.

Returning now to FIG. 2, in conjunction with FIG. 1a, which figure is a simplified flowchart 200 of a method for continuous monitoring and detection of changes in parameter values and corrective actions to the changes according to some embodiments of the present invention.

In a continuous monitoring step 202, the volumetric urine output of the kidneys is monitored using urine flow monitoring apparatus 130.

The urine flow monitoring apparatus 130 is typically connected between catheters 102, 104 and connection means 108. Apparatus 130 typically comprises a low flow metering device 106.

In especially preferred embodiments of the present invention said low flow metering device incorporates a drop generator and a droplet counter.

In a most preferred embodiment of the present invention, the present invention utilizes a modified version of the low flow metering device described and claimed in U.S. Pat. No. 6,640,649, the relevant teachings of which are incorporated herein by reference.

The absolute volumes and changes in the volume of urine over time are relayed from apparatus 130 to computer 140 and stored there in memory 146. Processing device 148 comprises software configured and operative to compare the volumetric urinary output at different times and to check if there is any change in an absolute volume value or in a trend of the output over time.

In a similar fashion, the analyte monitoring system 150 is configured and operative to continuously monitor analyte concentrations and quantities, as well as trends in changes of the analyte concentrations over time.

According to one embodiment electrode 110 monitors, for example, a dissolved oxygen concentration, and a dissolved oxygen concentration change in the urine over time. Electrode 112 monitors, for example, a sodium ion concentration, and a sodium ion concentration change in the urine over time.

Electrode 114 monitors a potassium ion concentration, and a potassium ion concentration change in the urine over time.

Electrode 116 monitors, for example, a pH value and a pH value change in the urine over time.

It should be understood that there are numerous combinations and permutations of possible configurations of apparatus 150 and correspondingly many combinations of parameters and urinary parameters that may be monitored over time.

As stated, according to the present invention, the parameters are measured at least semi-continuously.

According to some embodiments, at least some of the parameters are measured continuously or substantially continuously. "Continuously" means taking a reading of a parameter at least once a minute. "Substantially continuously" means taking a reading of the parameter at least once every five minutes.

According to some other embodiments the volumetric measurements of the urine are monitored continuously and only some of the other parameters are monitored continuously or substantially continuously.

Computer 140 is operative to continuously compare a newly acquired value of a parameter with the previous value. Additionally, a trend of the parameter over a fixed time interval is logged. For example, the urine flow may be determined every second. The trend of urine flow over a time period of one minute may be logged and shown on screen 142.

In a checking step 204, computer 208 is operative to check if there is a change in urine volume or trend, or a change in any other parameter or urinary parameter.

If not the computer proceeds to check signals received from the logging device of another parameter (such as the electronic input received from one of the electrodes), in a go to next parameter step 206.

If there is a change in a parameter value and/or a urinary parameter, computer 140 is operative to check the change against a preliminary diagnosis graph, such as seen in FIGS. 5-10, which will be programmed as an algorithm into the software of the computer.

Additionally or alternatively, a medical practitioner may perform this step manually.

If there is a specific change in a parameter value and/or trend, the computer may set off an alarm, such as if the urine flow suddenly stops.

Graphs 5-10 exemplify the combinations of various changes in one or more parameters or urinary parameters over time. These graphs will be expanded further to provide an analysis of all the different possible combinations and permutations of parameter changes and urinary parameter changes.

In a corrective action step 210, system 100 may automatically introduce the corrective action via computer 150 activating one or more systems linked to the patient (not shown). This may include a liquid infusion pump system, a blood transfusion pump; a drug injection device for direct injection into patient 101 or into the liquid infusion device.

Additionally or alternatively, a medical practitioner may provide the corrective action(s) and be prompted on screen 142.

Thus, the automation of the present invention involves checking the results provided by the system, noting if there is a problem that can be remedied by administration of a specific pharmaceutical, administering said pharmaceutical and then checking again to determine if the problem has been solved.

According to some embodiments, a combination of automated corrective actions and non-automated corrective actions (by a nurse or medical practitioner or by the patient himself) may be performed in this step.

In another checking step 212 an additional parameter may be checked by system 100 or by the nurse or medical practitioner. If the parameter is checked by the practitioner, for example, he may enter the data via inputting device 144 into memory 146 of computer 140. If logged automatically by computer 140, the data is automatically stored in memory 146 of computer 140.

In a second checking step 214, computer 140 is operative to check if there is a change in the additional parameter. If not, then the computer proceeds to check the next parameter in turn (step 206). If there is a change, then the computer proceeds to check the changes in the additional parameter against the preliminary diagnosis algorithms.

Reference is now made to FIG. 3, which is a simplified flowchart 300 of a method for continuous monitoring and detection of changes in urinary parameters and corrective actions to the trend changes according to some embodiments of the present invention.

In a continuous monitoring step 302, the volumetric urine output trend over time of the kidneys is monitored using urine flow monitoring apparatus 130.

The urine flow monitoring apparatus 130 is typically connected between catheter 102 and connection means 108. Apparatus 130 typically comprises a low flow metering device 106.

In especially preferred embodiments of the present invention said low flow metering device incorporates a drop generator and a droplet counter.

The trend of changes in the volume of urine over time are relayed from apparatus 130 to computer 140 and stored there in memory 146. Processing device 148 comprises software configured and operative to compare the volumetric urinary output at different times and to check if there is any change in an absolute volume value or in a trend of the output over time.

In a similar fashion, the analyte monitoring system 150 is configured and operative to continuously monitor analyte concentrations and quantities, as well as trends in changes of the analyte concentrations over time.

According to one embodiment micro-, mini- or macro-electrode 110 monitors, for example, a dissolved oxygen concentration, and a dissolved oxygen concentration change in the urine over time. Electrode 112 monitors, for example, a sodium ion concentration, and a sodium ion concentration change in the urine over time.

Electrode 114 monitors, a potassium ion concentration, and a potassium ion concentration change in the urine over time.

Electrode 116 monitors, for example, a pH value and a pH value change of the urine over time.

It should be understood that there are numerous combinations and permutations of possible configurations of apparatus 150 and correspondingly many combinations of parameters and urinary parameters that may be monitored over time.

Computer 150 is operative to continuously compare a newly acquired trend of a parameter with the previous trend over identical periods of time. For example, the urine flow may be determined every second. The trend of urine flow over a time period of one minute may be logged and shown on screen 142.

In a checking step 304, computer 308 is operative to check if there is a change in urine trend over two consecutive minutes, for example, or a change in any other urinary parameter.

If not, the computer proceeds to check signals received from the logging device of another urinary parameter (such as the electronic input received from one of the electrodes), in a go to next urinary parameter step 306.

If there is a change in a urinary parameter, computer 140 is operative to check the change against a preliminary diagnosis algorithm which are based on graphs 7-10.

Additionally or alternatively, a medical practitioner may perform this step manually.

If there is a specific change in a urinary parameter, the computer may set off an alarm, such as if the urine flow suddenly is reduced by more than 20%.

It is to be noted that the method and system of the present invention can also be utilized and set to recognize at least one change in a urinary parameter trend, such as a dynamic trend indicative of a body malfunction.

In a corrective action step 310, system 100 may automatically introduce the corrective action via computer 140 activating one or more systems linked to the patient (not shown). This may include a liquid infusion pump system, a blood transfusion pump; a drug injection device for direct injection into patient 101 or into the liquid infusion device.

Additionally or alternatively, a medical practitioner may provide the corrective action(s) and be prompted on screen 142.

According to some embodiments, a combination of automated corrective actions and non-automated corrective actions (by a nurse or medical practitioner or by the patient himself) may be performed in this step.

In another checking step 312 an additional urinary parameter may be checked by system 100 or by the nurse or medical practitioner. If the parameter is checked by the practitioner, for example, he may enter the data via inputting device 144 into memory 146 of computer 140. If logged automatically by computer 140, the data is automatically stored in memory 146 of computer 140.

In a second checking step 314, computer 140 is operative to check if there is a change in the additional urinary parameter. If not, then the computer proceeds to check the next urinary parameter in turn (step 306). If there is a trend change, then the computer proceeds to check the changes in the additional parameter against the preliminary diagnosis algorithms.

Figure 12A:
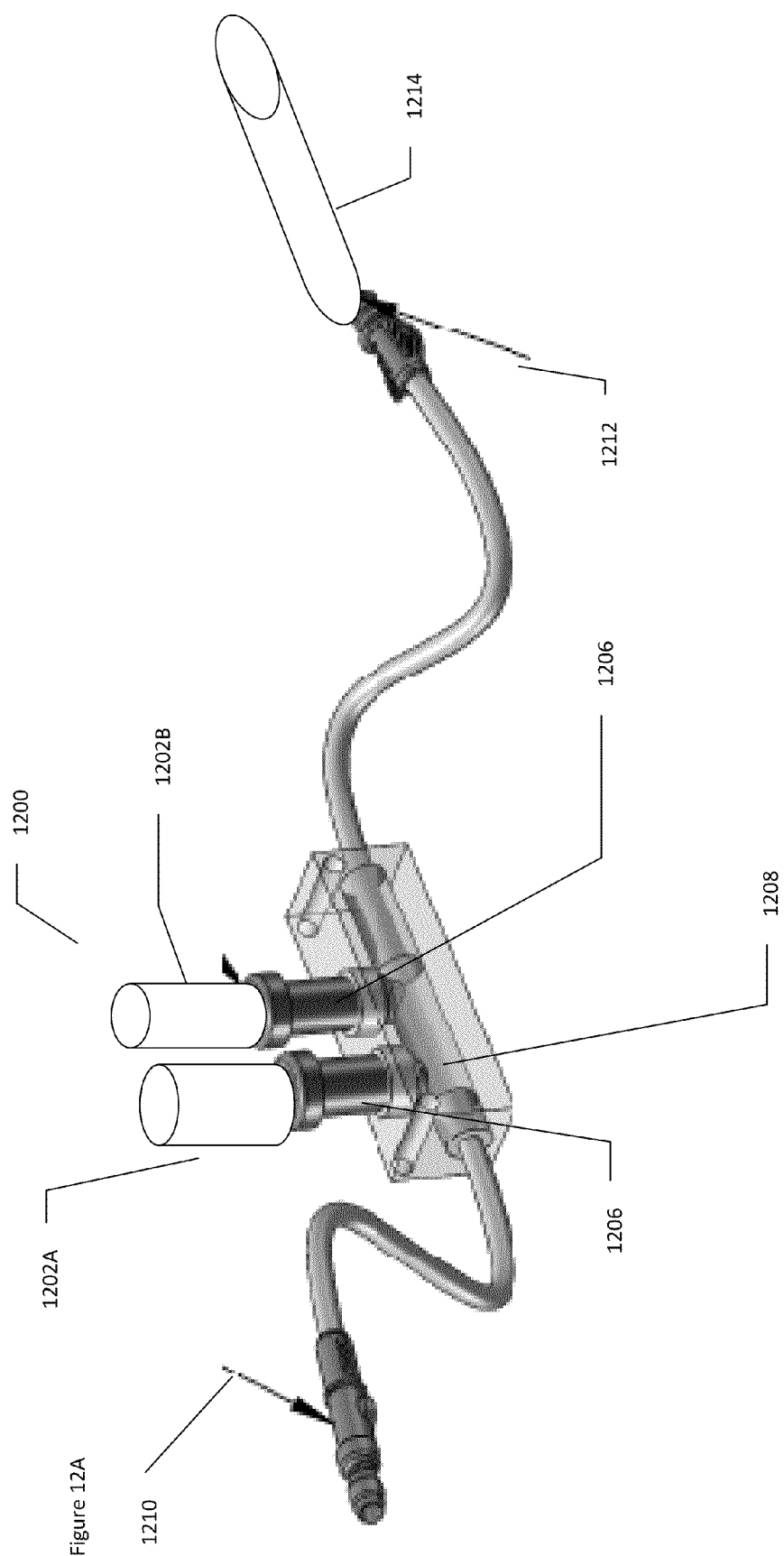

The above described analyte monitoring system may optionally feature one or more electrodes for continuously monitoring one or more analytes in urine flow. The electrodes are preferably oriented perpendicularly to the flow of urine, as shown in an electrode system in FIGS. 12A and 12B. FIG. 12A shows an exemplary electrode system 1200 for use with the analyte monitoring system 150 of FIG. 1A, for continuously monitoring corresponding one or more analytes. A plurality of electrodes 1202 is used, of which two electrodes 1202 are shown for the purpose of illustration and without wishing to be limiting in any way. In this non-limiting example, electrodes 1202 are arranged for potentiometry, with a reference electrode 1202A and a glass membrane electrode 1202B. Electrodes 1202 are arranged within an electrode holder 1204, with two electrode sockets 1206, to be perpendicular to the flow of urine. Electrode holder 1204 features an enclosed chamber 1208 within which measurements are made, as the urine contacts electrodes 1202.

Urine flows from a catheter connector 1210, through electrode holder 1204 for measurement(s) and then exists through a tube connector 1212 that connects the flow to a urine bag or other arrangement, preferably to a negative pressure flow tube 1214, for example as described with regard to U.S. patent application Ser. No. 12/669,494, filed on Jul. 16, 2008, by at least one of the present inventors and owned in common with the present application, hereby incorporated by reference as if fully set forth herein, for optionally and preferably providing continuous flow of urine.

Although monitoring systems are known for fluids, urine is an unusual fluid in that it is a colloid. As such, regular fluid monitoring systems are not effective, since the materials in the colloid, such as proteins for example, would be expected to foul the electrodes. Other known urine monitoring systems do not teach any particular orientation of the electrodes as being important or useful for monitoring. Without wishing to be limited by a closed list, such art known systems do not feature orientation of the electrodes in a perpendicular manner with regard to the urine flow, nor do they feature the ability to provide continuous flow of urine, for example through negative pressure flow tube 1214.

The above arrangement was tested for one element, namely sodium, to determine whether viable, accurate readings could be determined within a closed chamber, for example enclosed chamber 1208. Furthermore, the arrangement was also tested to determine whether the electrodes 1202 could be maintained on line for a reasonable period of time and in use without "reconditioning" (a technical term for refreshing the electrodes back to a clean state and recalibrating them), and to observe how the electrode reacted over a period of time to contamination.

In addition the boundary effects for the electrodes were observed as well as the stability of readings and accuracy. General practical parameters were observed including orientation of the electrodes in the flow, need for calibration or recalibration etc, all of which were found to be stable and within useful boundaries for practical real world use. It was found that this arrangement could in fact provide reasonable readings with correctable or predictable results.

The above mentioned embodiments may also optionally feature color detection, particle size detection and cloudiness determination. For example, as shown with regard to FIG. 12B, electrode system 1200 (from FIG. 12A but shown as a single box for the sake of clarity) preferably features one or more sensors, of which a color sensor 1250 is shown. Color sensor 1250 may optionally combine photodiodes and color filters eg integrated color sensors from TAOS combine a photodiode, color filter, and transimpedance amplifier on a single die. The output is then fed to an ADC (analog to digital converter) for digital processing, for example by a microprocessor.

Optionally a turbidity detector 1252 is also included. Turbidity (cloudiness) detection may be provided eg by using a dual beam ratio method or a modulated four beam method, with light sensors and emitters around a transparent section of tube at the relevant angles.

Also optionally a particle size detector 1254 is included. Particle size analysis can be performed eg using optical methods outside a transparent section of pipe using for example light scattering or laser diffraction, such that the light source and detector are placed at relevant positions and angles outside the pipe section.

Optionally a single electrode system could be implemented as for the above (not shown). Also optionally, rather than continuous flow, or in combination with continuous flow, the above measurements are performed with stop/start or discontinuous flow.

Figure 13:
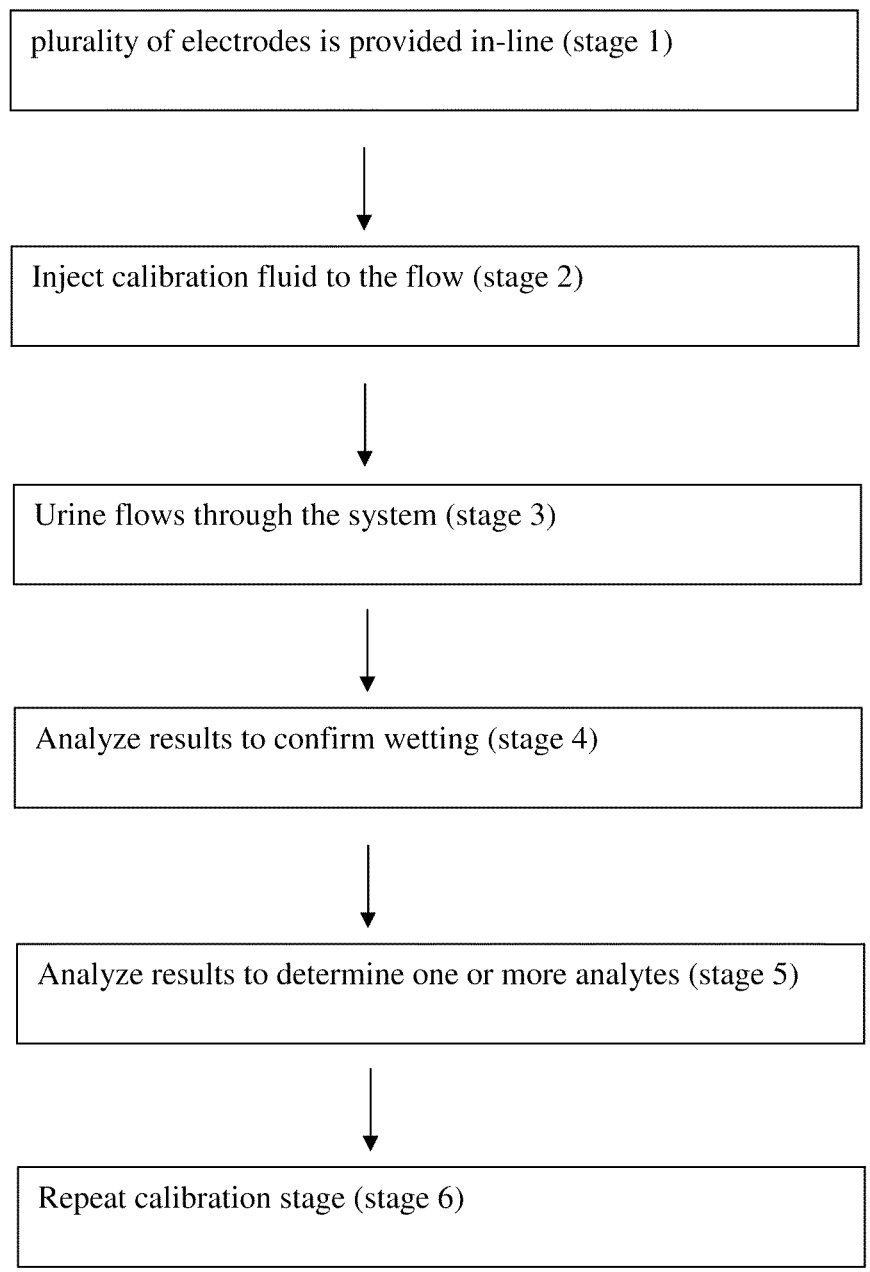
FIG. 13 shows a flowchart of an exemplary method according to at least some embodiments of the present invention, featuring in-line flow continuous monitoring of one or more analytes through a plurality of electrodes.

FIG. 13 shows a flowchart of an exemplary method according to at least some embodiments of the present invention, featuring in-line flow continuous monitoring of one or more analytes through a plurality of electrodes, as described for example with regard to FIG. 12.

In stage 1, a plurality of electrodes is provided in-line within the flow, perpendicular to the flow, and is connected to the patient's urine catheter system, however preferably without permitting urine to flow past the electrodes.

In stage 2, a calibration process is preferably performed before any readings are taken, for example optionally and preferably by using a kit with a correct quantity of saline fluid which would be injected into the manifold (ie chamber containing the electrodes). One or more calibration readings are then preferably performed before commencing urine flow. Optionally, additionally or alternatively, a calibration fluid is injected to the urine flow and the results are determined for calibration.

In stage 3, urine is permitted to flow through the system, past the electrodes and one or more readings are performed. In stage 4, the results are optionally analyzed to confirm wetting or adequate urine flow or urine level. In stage 5, the results are optionally further analyzed to determine the level of one or more analytes, according to the previous calibration and also according to the level of wetting. Optionally, the calibration stage is repeated at least once more during the above process, in stage 6. Stages 1-6 may optionally be repeated one or more times.

Thus, the method of the present invention provides an invaluable tool for early detection of abnormal conditions not provided by the standard measuring tools available today.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A monitoring apparatus for at least semi-continuous real-time in-line monitoring of urine from a patient, the patient having a catheter inserted therein, the catheter having a distal portion extending outside of the patient, the apparatus comprising: a catheter tube fluidly connected to said distal portion; an electrode system fluidly connected to said catheter tube, said electrode system comprising a receiving connector for fluidly connecting to said catheter tube, and a chamber fluidly connected to said receiving connector, said chamber comprising at least one glass electrode arranged perpendicularly to a flow of urine through said chamber, wherein said at least one electrode operates without reconditioning, wherein said catheter tube comprises a negative pressure tube for providing continuous flow of urine through said chamber, wherein said flow of urine flows directly from the patient through the catheter, through said catheter tube, into said receiving connector and into said chamber for in-line analysis without interruption.

2. The apparatus of claim 1, comprising a plurality of electrodes arranged perpendicularly to the flow of urine in said chamber.

3. The apparatus of claim 2, wherein said electrodes are arranged to measure one or more of sodium, potassium, oxygen, pH or a combination thereof.

4. The apparatus of claim 3, wherein said electrode system further comprises a measurement reader for determining a measurement of said one or more of sodium, potassium, oxygen, pH or a combination thereof.

5. The apparatus of claim 4, wherein said measurement reader further comprises a computational processor for processing said measurement.

6. The apparatus of claim 5, wherein said computation processor also processes said measurement according to a calibration reading.

7. The apparatus of claim 6, wherein said electrode system further comprises a color detector.

8. The apparatus of claim 7, wherein said electrode system further comprises a turbidity detector.

9. The apparatus of claim 8, wherein said electrode system further comprises a particle size detector.

10. A diagnostic method for detecting at least one change in a urinary parameter indicative of a body malfunction, the method comprising at least semi-continuously monitoring in real time at least one of a sodium level, an oxygen level, a potassium level, and combinations thereof in the urine of a catheterized patient; whereby at least one parameter is monitored so as to detect one or more changes in the at least one parameter to reflect at least one of a fluid state, an electrolyte balance, a kidney state, a kidney perfusion and an organ perfusion in the patient, indicative of the body malfunction in the patient, wherein the monitoring comprises arranging electrodes perpendicularly to and in the flow of urine through a patient's catheter system, in line to said system, wherein said electrodes comprise a glass electrode; receiving urine from the patient to said electrodes; and analyzing said one or more levels in real time by said electrodes at least once every five minutes without interruption to the flow of urine.

11. The method of claim 10, wherein said analyzing said one or more levels is performed at least once every minute.

12. The apparatus of claim 1, wherein said in-line analysis is performed at least once every minute.

13. The method of claim 10, wherein said monitoring comprises performing calibration once before analyzing said one or more levels in real time over a period of elapsed time.

14. The apparatus of claim 1, wherein said in-line analysis requires calibration once.

15. The apparatus of claim 1, wherein said chamber is a flow compensated chamber.

16. The apparatus of claim 1, wherein said at least one glass electrode comprises a glass membrane electrode.

17. The method of claim 10, wherein said at least one glass electrode comprises a glass membrane electrode.

18. The method of claim 17, wherein said electrodes operate without reconditioning.

19. A monitoring apparatus for in-line monitoring of urine from a patient, the patient having a catheter inserted therein, the catheter having a distal portion extending outside of the patient, the apparatus comprising: a catheter tube fluidly connected to said distal portion; an electrode system fluidly connected to said catheter tube, said electrode system comprising a receiving connector for fluidly connecting to said catheter tube, and a chamber fluidly connected to said receiving connector, said chamber comprising at least one electrode arranged perpendicularly to a flow of urine through said chamber, wherein the tip of said electrode is immersed in said flow of urine, wherein said flow of urine flows directly from the patient through the catheter, through said catheter tube, into said receiving connector and into said chamber for in-line analysis without interruption, wherein said chamber further comprises a negative pressure flow tube to provide flow compensation.

* * * * *